(12) United States Patent
Eikje

(10) Patent No.: US 10,925,521 B2
(45) Date of Patent: Feb. 23, 2021

(54) FORMULA AND METHOD FOR MONITORING INDIVIDUAL METABOLIC RESPONSE AND FOR GENERATING PREDICTIVE MEDICAL METRICS

(71) Applicants: MC Professional OU, Tallinn (EE); Irina Skrebova, Tallinn (EE); Natalja Eikje, Tysvaervaag (NO)

(72) Inventor: Natalja Eikje, Tysvaervaag (NO)

(*) Notice: Subject to any disclaimer, the term of this patent is extended or adjusted under 35 U.S.C. 154(b) by 51 days.

(21) Appl. No.: 14/376,581

(22) PCT Filed: Feb. 21, 2013

(86) PCT No.: PCT/EE2013/000002
§ 371 (c)(1),
(2) Date: Oct. 16, 2019

(87) PCT Pub. No.: WO2013/135249
PCT Pub. Date: Sep. 19, 2013

(65) Prior Publication Data
US 2020/0245909 A1    Aug. 6, 2020

Related U.S. Application Data

(60) Provisional application No. 61/596,250, filed on Feb. 21, 2012.

(51) Int. Cl.
*A61B 5/145*    (2006.01)
*G16H 50/30*    (2018.01)
(Continued)

(52) U.S. Cl.
CPC ........ *A61B 5/14532* (2013.01); *A61B 5/1455* (2013.01); *A61B 5/4866* (2013.01);
(Continued)

(58) Field of Classification Search
CPC ......... A61B 5/145; A61B 5/00; A61B 5/1455; A61B 5/4866; A61B 5/7257; A61B 5/14532; G16H 50/20; G16H 50/30
See application file for complete search history.

(56) References Cited

U.S. PATENT DOCUMENTS 6,718,189 B2   4/2004   Rohrscheib
2003/0191377 A1   10/2003   Rohrscheib

OTHER PUBLICATIONS

Natalja Skrebova Eikje, "Lag time changes between capillary blood glucose and in-vivo interstitial glucose levels by HATR-FTIR spectroscopy," Proc.SPIE 7898, Dynamics and Fluctuations in Biomedical Photonics VIII, 78980S (Feb. 10, 2011); doi: 10.1117/12.874716 (Year: 2011).*

(Continued)

*Primary Examiner* — Eric J Messersmith
(74) *Attorney, Agent, or Firm* — D'Hue Law LLC; Cedric A. D'Hue

(57) ABSTRACT

Provided is a formula and method for monitoring individual metabolic response that involve calculation of the lag/latency time (LT) for the peak levels of measured a variety of glucose values by HATR-FTIR (horizontally attenuated total reflection Fourier transform infrared) spectroscopy and the LT for the peak level of capillary blood glucose (CBG), with subsequent calculation of the LT changes between them. Obtained meaningful time-dependent and dose-dependent glucose values and their LT changes characterize glycemic variability (GV) in a qualified subject, that can be used to predict the patient's risk of hyperglycemia, to stage Type II diabetes and, in general, to be considered as a new metrics of assessing the quality of metabolic control.

12 Claims, 21 Drawing Sheets

(51) Int. Cl.
    *G16H 50/20*     (2018.01)
    *A61B 5/1455*     (2006.01)
    *A61B 5/00*     (2006.01)

(52) U.S. Cl.
    CPC ........... *A61B 5/7257* (2013.01); *G16H 50/20* (2018.01); *G16H 50/30* (2018.01)

(56) References Cited

OTHER PUBLICATIONS

Eikje Natalja Skrebova, "Diabetic Interstitial Glucose by ATR-FTIR Spectroscopy Versus Capillary Blood Glucose", Blood Glucose, Apr. 1, 2010, pp. 81-90, vol. 3, No. 2, Journal of Innovative Optical Health Sciences (JIOHS), World Scientific Publishing, Singapore, available at doi:10.1142/S1793545810000903.

Applicant, Amended claims to Korean national stage patent application serial No. 10-2014-7026501, Sep. 16, 2019, 24 pages.
WIPO, Written Opinion of the International Searching Authority for PCT international patent application serial No. PCT/EE2013/00002, dated Jan. 8, 2014, 7 pages.
WIPO, International Search Report for PCT international patent application serial No. PCT/EE2013/00002, dated Jan. 8, 2014, 7 pages.
WIPO, International Preliminary Report on Patentability for PCT international patent application serial No. PCT/EE2013/00002, dated Aug. 26, 2014, 8 pages.
Korean Intellectual Property Office, Notification of Provisional Rejection, dated Mar. 16, 2019.
Applicant, English description of Notification of Provisional Rejection, dated Apr. 16, 2019, 5 pages.
Applicant, English description of Notification of Provisional Rejection, dated Apr. 16, 2019, 3 pages.

\* cited by examiner

FORMULA AND METHOD FOR MONITORING INDIVIDUAL METABOLIC RESPONSE AND FOR GENERATING PREDICTIVE MEDICAL METRICS

BACKGROUND OF THE INVENTION

Field of the Invention

The invention relates generally to monitoring metabolic response in a qualified subject, that comprises the step of consecutive performance of a plurality of measurements and further calculations of glucose levels, obtained by HATR-FTIR (horizontally attenuated total reflection Fourier transform infrared) spectroscopy. More particularly, the invention further relates to a formula for calculating the lag/latency time (LT) changes between measured in capillary blood the peak glucose level and by HATR-FTIR spectroscopy the peak levels of glucose values after achieved response in test subjects' from the ingestion of quantified amount of pure glucose and post-prandially, allowing to assess stability of metabolic control in healthy, prediabetic and diabetic subjects. Furthermore, qualitative and quantitative interpretation of glycemic variability (GV) by using a formula for calculation of the LT changes, based on a method of simultaneous assessment of 5 glucose-specific values by HATR-FTIR spectroscopy, helps to generate parameters, their characteristics, patterns and, thus, to establish suitable metrics for GV in the clinical practice.

Description of the Related Art

There are numerous published metrics to quantify different aspects of GV, but still there is no method of GV that is accepted in the clinical practice of diabetes care.

Developing a new set of metrics to evaluate normal, as well as clinically relevant high and low interstitial glucose levels might open for clinicians a new way in the interpretation of the activity of glucose metabolism for diagnosis, treatment and management of the patients with diabetes mellitus and carbohydrate metabolism disorders.

The technique of using ATR-FTIR spectroscopy has been long known for non-invasive glucose measurement, but through oral mucosa. The drawbacks of such measurements included glucose contamination of the measurement site by food and a highly variable rate of saliva.

Attempts have been made to demonstrate a proof of HATR-FTIR spectroscopy technique to detect, characterize and verify interstitial origin of glucose-specific signals at about 1030, 1041, 1080, 1118 and 1153 $cm^{-1}$ in the skin of healthy, prediabetic and diabetic subjects during OGTT (Oral Glucose Tolerance Test) and post-prandially, randomly and on mornings, i.e. fasting measurements.

Carbohydrate intolerance is one of the major criteria for a diagnosis of diabetes mellitus. OGTT employs ingested carbohydrate in a predetermined form and an amount to quantify a test subject's response to a resulting glucose challenge. However, this test is only concerned with the peak blood level of glucose, but not with the rate of change in glucose levels or the amount of time it takes for glucose levels to fluctuate from a high point to a lower point.

The medical significance of blood glucose fluctuations, i.e. frequency and magnitude, has been a controversial topic and the subject of extensive research, proving that GV can be used to describe a general risk of hyperglycemia over long periods of time, or when focused on events of short duration, such as meals or overnight.

Since glucose on the surface of the skin and within the stratum corneum has been considered as a source for extraneous glucose contamination during testing of invasive glucose monitoring devices, there was not found any direct method for in vivo glucose molecule(s) characterization and monitoring directly on healthy, prediabetes and diabetes subjects.

SUMMARY OF THE INVENTION

An object of the present invention is to provide the user with in vivo method for monitoring individual metabolic response and a formula for qualitative and quantitative characterization of GV, in order to further recognize patterns from the patients data for establishing predictive clinical metrics.

Specifically, the invented method is based on a formula for calculating the LT changes between the LT measured for the peak of CBG and the LT for the peaks of epidermally measured interstitial glucose levels by HATR-FTIR spectroscopy on healthy, prediabetic and diabetic subjects under OGTT with different doses (low, medium, high) and post-prandially, applicable for staging Type 2 diabetes and assessing diabetes control, including estimation of intra-day and intra-week risks, as well a general risk of hyperglycemia. More, the invented formula can be further applied for screening of disorders of glucose metabolism, such as impaired glucose tolerance and diabetes mellitus by means of evaluation of the time required for glucose to diffuse from the capillary to the living skin tissue. In addition, the invented formula can be also served for individual calibration of obtained glucose profiles by HATR-FTIR spectroscopy in a dynamic time-dependent manner in a qualified subject.

BRIEF DESCRIPTION OF THE TABLES

Table 1. LT changes estimated within a 120-minute post-prandial monitoring of metabolic response in 3 subjects with Type 2 diabetes (S1, S2 and S3) by HATR-FTIR spectroscopy.

Table 2. LT changes between the LT for the peak of CBG and the LT peak for each measured glucose level at about 1030, 1041, 1118 and 1153 cm$^{-1}$, obtained in a healthy subject during OGTT at different doses (5 g, 20 g, 75 g).

Table 3. LT changes between the LT for the peak of CBG and the LT peak for each measured glucose level at about 1030, 1041, 1118 and 1153 cm$^{-1}$, obtained in a diabetic subject during OGTT at different doses (5 g, 20 g, 75 g).

Table 4. LT changes under OGTT with 75 g., i.e. clinical, a healthy subject vs. a subject with Type 2 diabetes.

Table 5. LT changes under OGTT with 20 g., i.e. clinical, a healthy subject vs. a subject with Type 2 diabetes.

Table 6. LT changes estimated for the same subject with Type 2 diabetes on 2 consecutive days.

Table 7. OGTT (75 g), i.e. clinical OGTT, demonstrate estimated LT changes for healthy, prediabetic and diabetic subjects.

DETAILED DESCRIPTION OF THE EMBODIMENT

As described further herein, in vivo glucose spectral measurements from the skin surface of the inner wrists of measured subjects have been performed on a commercially available FT-IR spectrometer (Shimadzu IRPrestige—21/8400S, Japan), that measures the absorbance spectra in the 700-4000 cm$^{-1}$ region at a resolution of 4 cm$^{-1}$, using 20 frames of accumulation to collect interferogram. Non-invasive glucose monitoring is achieved by tight contact of the measured site with a specially designed flat-plated prism with a mounted ATR crystal for the PIKE Technologies Horizontal accessory (ATR-8200 HA). This horizontal accessory is of a trapezoid shape with carefully chosen dimensions by a manufacturer (80×10×4 cm), in order to maximize S/N ratio in the measured spectra.

A portable glucosemeter (SKK GluTestS, Sanwa Chemical Institute, Nagoya, Japan) has been used for CBG determinations in mg/dL.

Noninvasive spectroscopic interstitial glucose monitor to an individual necessitates a calibration. Generating such a calibration requires reference CBG values that are uncorrelated to sampling factors. The invented formula provides a method to calibrate dynamic measurements of interstitial glucose values in vivo by HATR-FTIR spectroscopy, based on referenced CBG values, that are described in FIG. 1.

A test subject's CBG values are controlled or manipulated through the oral ingestion of carbohydrate, i.e. meals, and/or through oral consumption of dissolved in water pure glucose at different determined doses (f.e. 5 g, 20 g, 75 g) in such a way that the changes of the targeted glucose profiles of FIGS. 1-4 are reproduced by the subject's own glucose profiles. Thus, since the subject's CBG is under active control, the influence of other sampling factors are eliminated.

Figure 1:
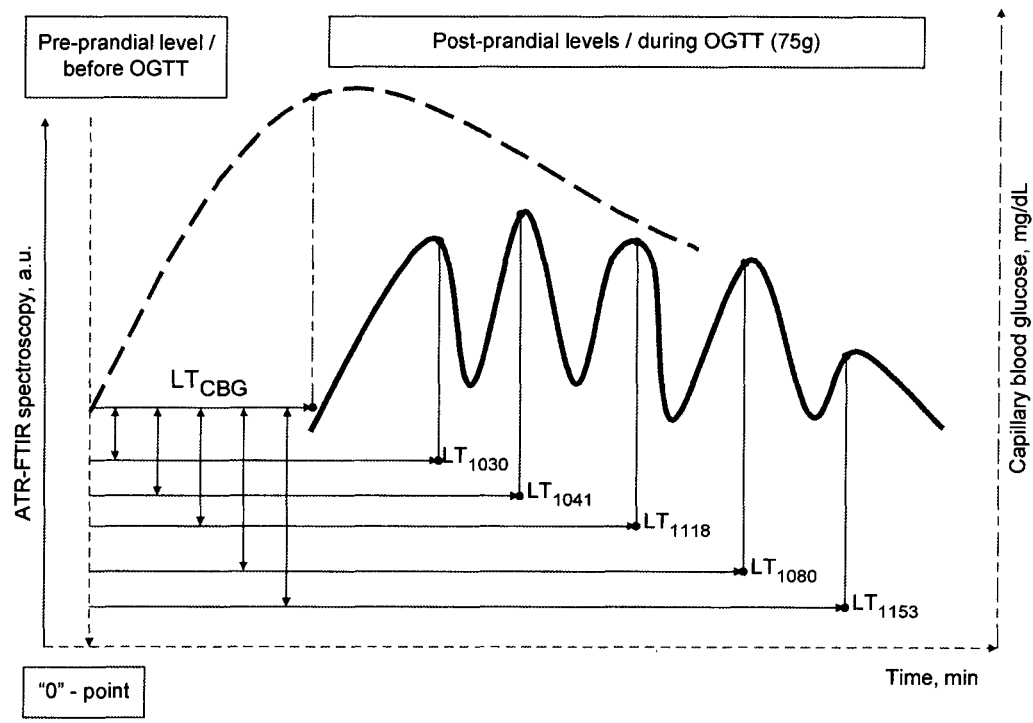
FIG. 1 schematically presents a formula and method for calculation of the LT changes between the LT for the peak of CBG and for the peak of each epidermally measured interstitial glucose level at about 1030, 1041, 1080, 1118 and 1153 $cm^{-1}$ by HATR-FTIR spectroscopy in a qualified subject.
Figure 2A:
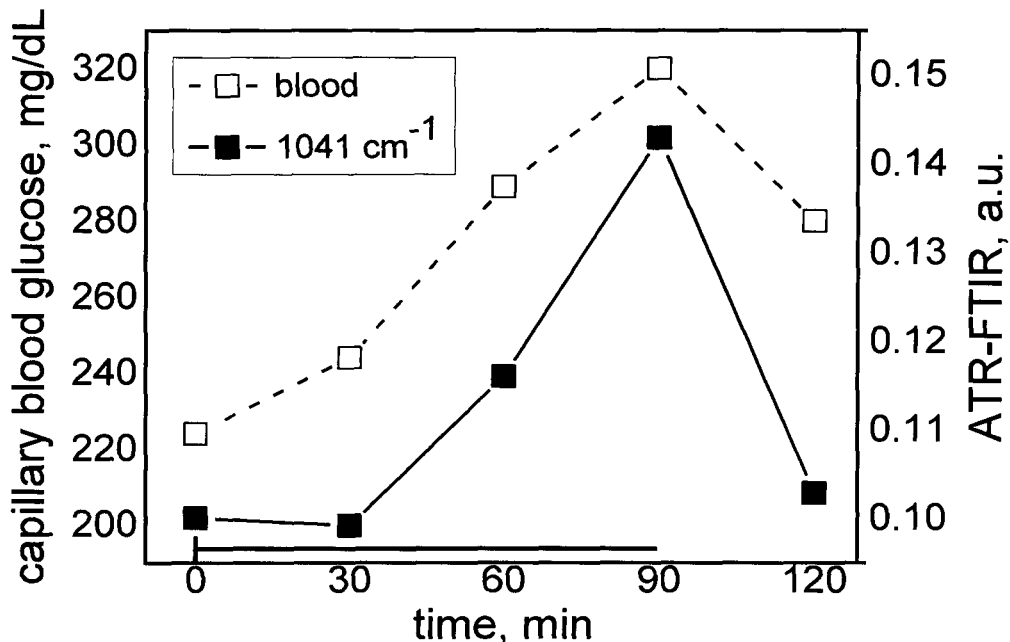
FIG. 2 A-D presents differences between GV obtained between CBG values (shown by dashed lines) and each glucose value (shown by solid lines) at about 1030, 1041, 1118 and 1153 $cm^{-1}$ by HATR-FTIR spectroscopy during a 120-minute post-prandial monitoring of individual metabolic response in Subject 1 with Type 2 diabetes. The time of increment for each glucose value is indicated by a solid line along x-axis. In case of a biphasic increase, a first phase is indicated by a dashed line along x-axis.
Figure 2B:
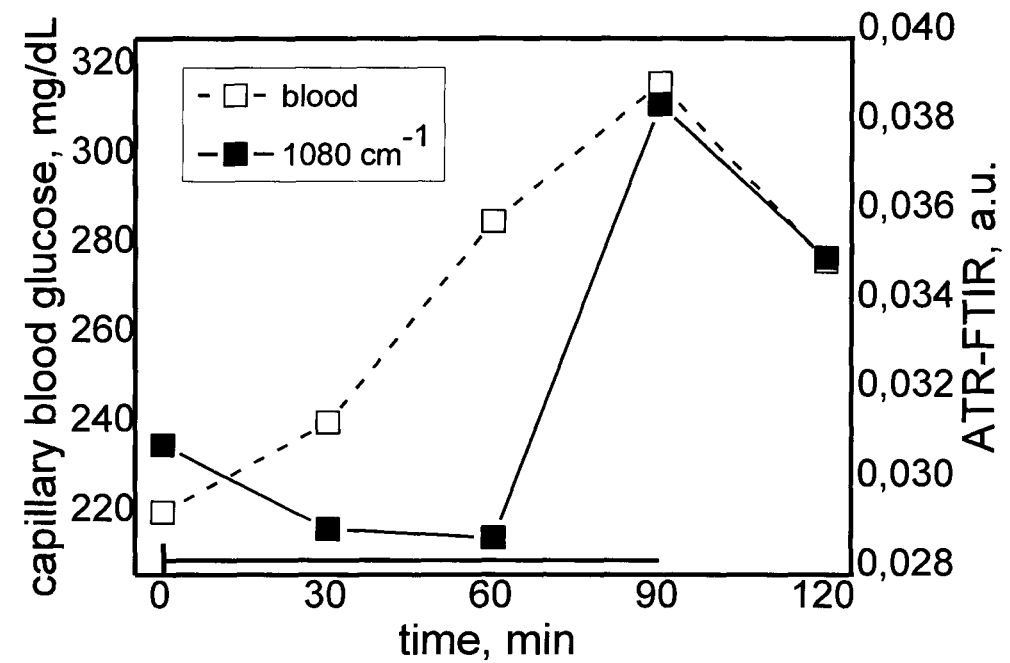
Figure 2C:
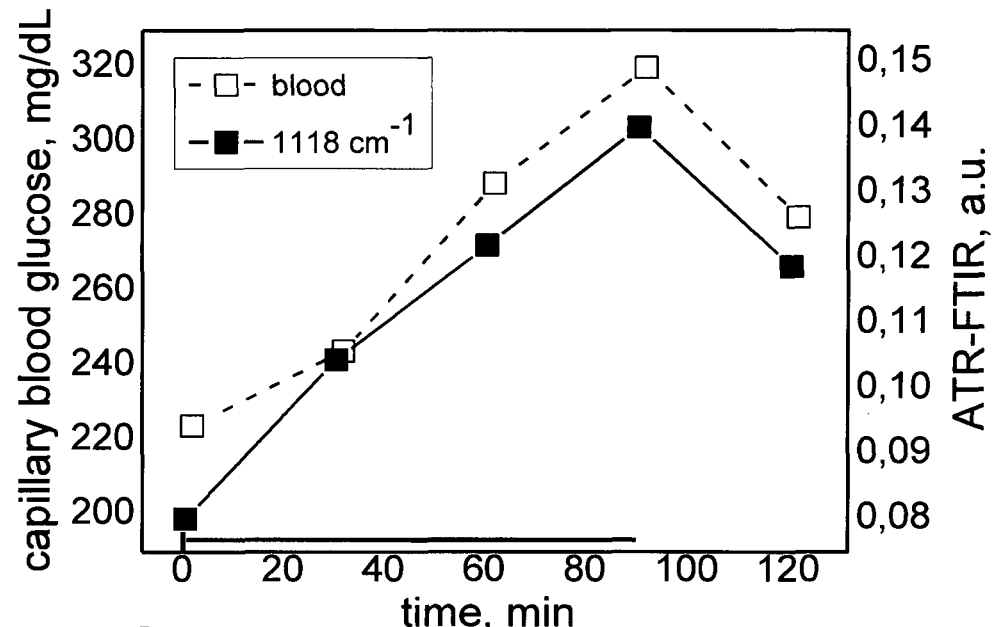
Figure 2D:
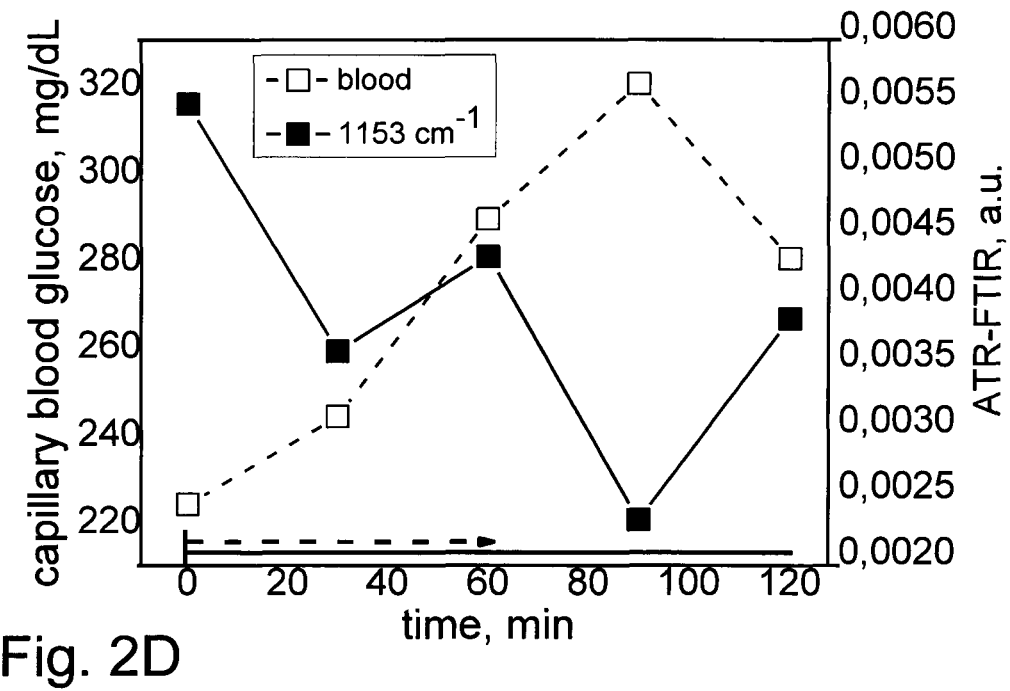
Figure 3A:
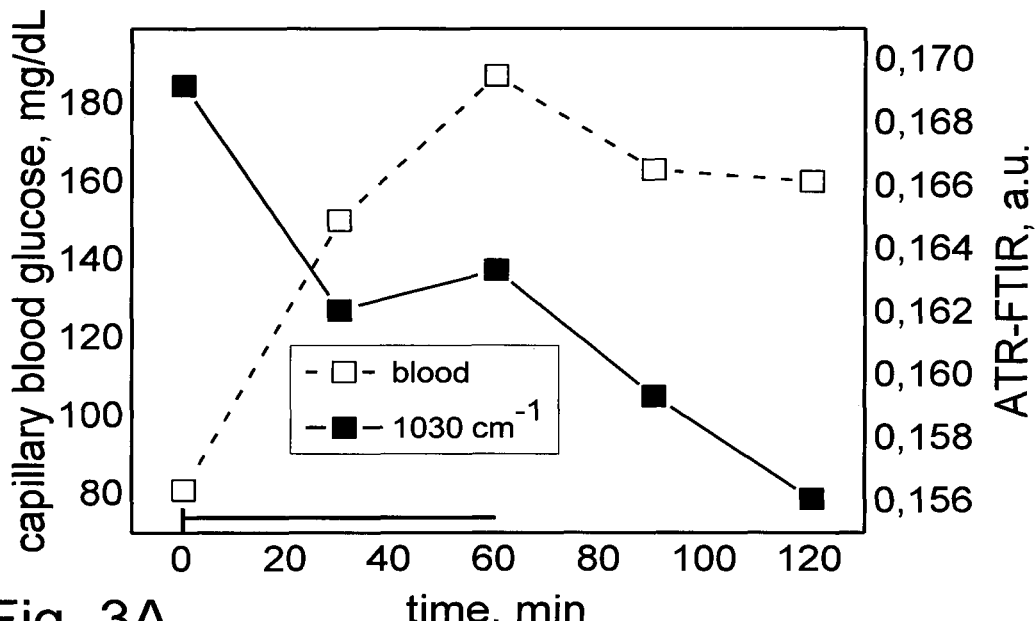
FIG. 3 A-D presents differences between GV obtained between CBG values (shown by dashed lines) and each glucose value (shown by solid lines) at about 1030, 1041, 1118 and 1153 $cm^{-1}$ by HATR-FTIR spectroscopy during a 120-minute post-prandial monitoring of individual metabolic response in Subject 2 with Type 2 diabetes. The time of increment for each glucose value is indicated by a solid line along x-axis. In case of a biphasic increase, a first phase is indicated by a dashed line along x-axis.
Figure 3B:
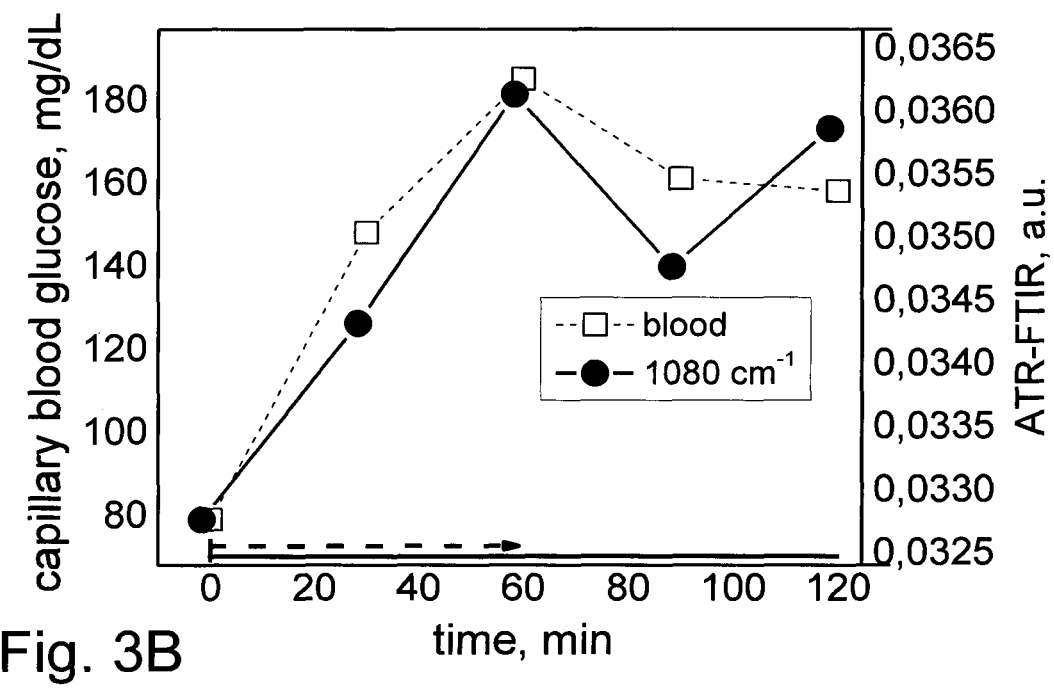
Figure 3C:
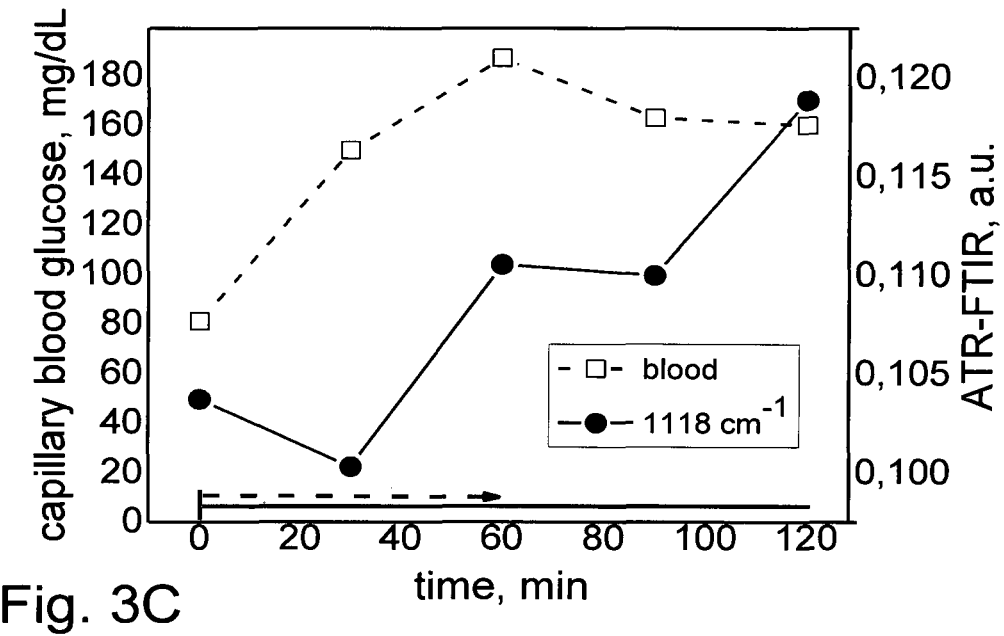
Figure 3D:
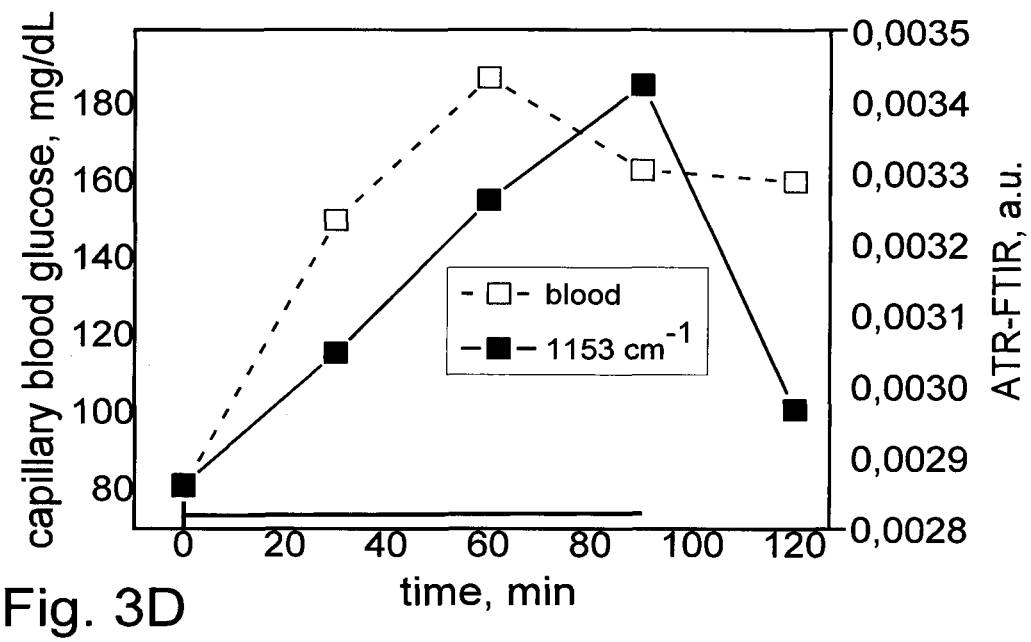
Figure 4A:
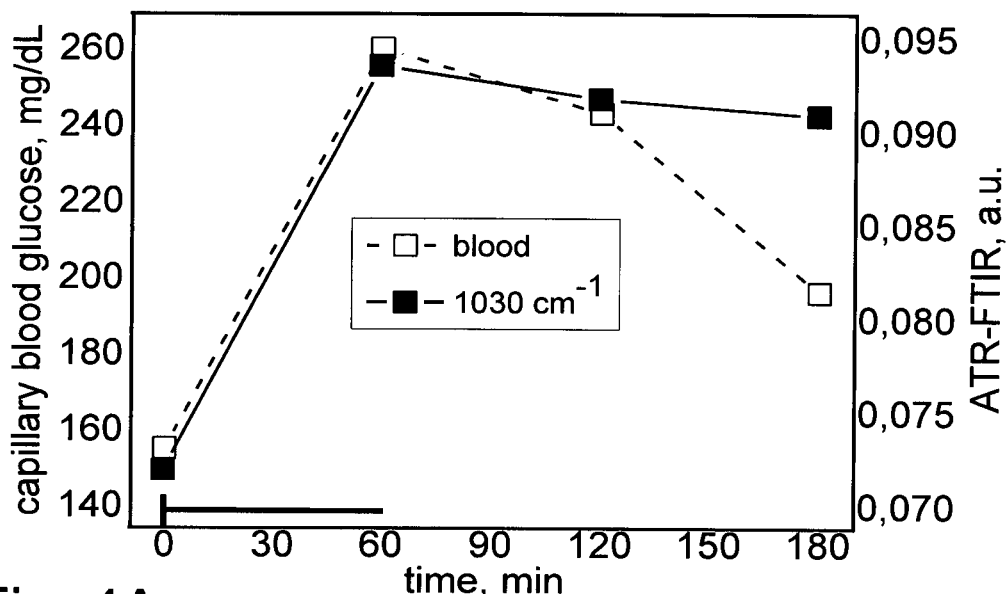
FIG. 4 A-D presents differences between GV obtained between CBG values (shown by dashed lines) and each glucose value (shown by solid lines) at about 1030, 1041, 1118 and 1153 $cm^{-1}$ by HATR-FTIR spectroscopy during a 120-minute post-prandial monitoring of individual metabolic response in Subject 3 with Type 2 diabetes. The time of increment for each glucose value is indicated by a solid line along x-axis. In case of a biphasic increase, a first phase is indicated by a dashed line along x-axis.
Figure 4B:
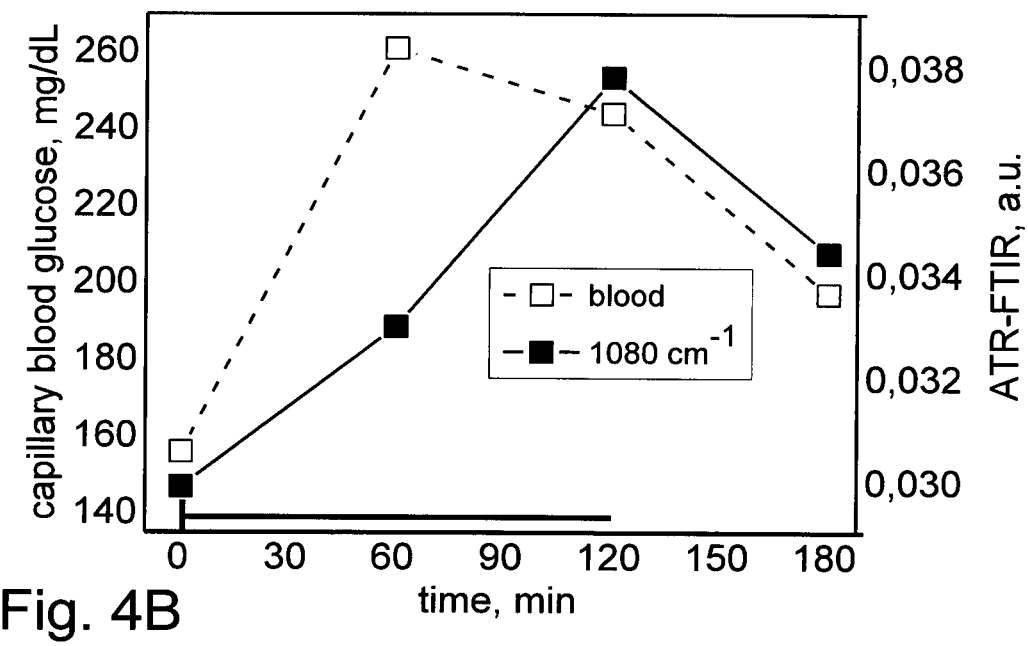
Figure 4C:
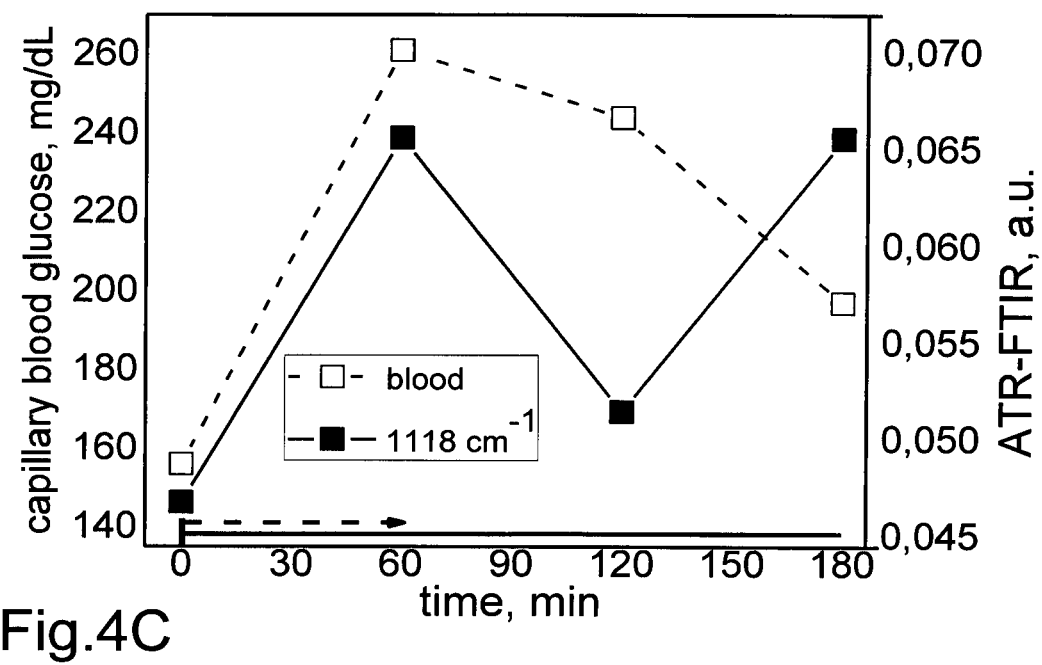
Figure 4D:
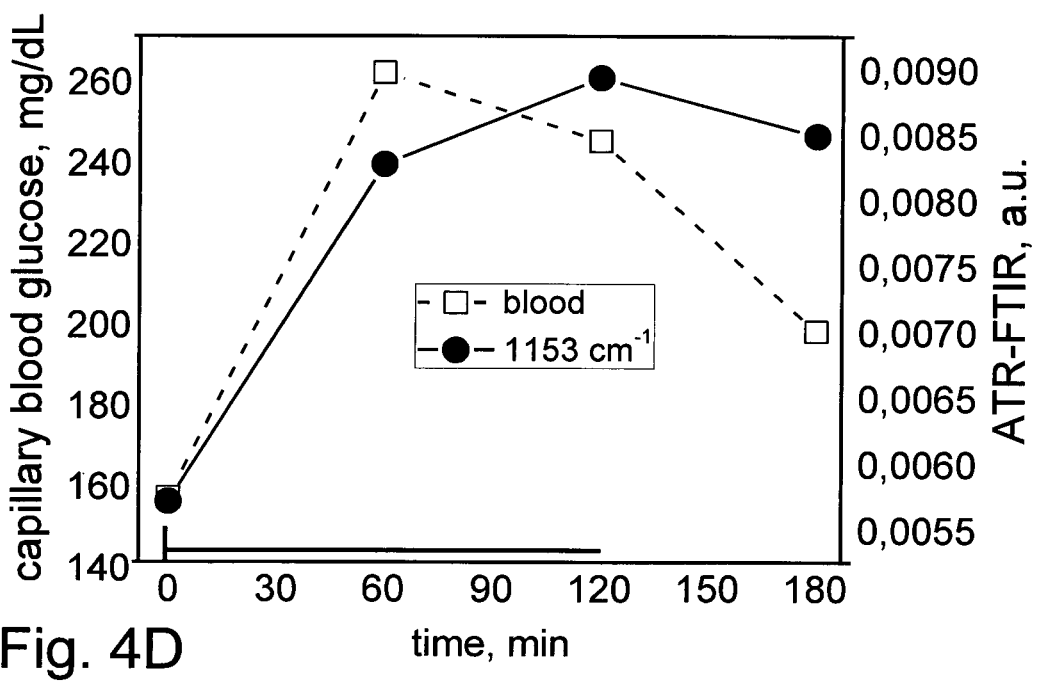

Steps of the invented formula and method:
performing reference CBG measurements at pre-determined intervals prior to spectral acquisition by HATR-FTIR spectroscopy
gathering in vivo HATR-FTIR spectra from the forearm of a tested subject at predetermined intervals in the 700-4000 cm$^{-1}$ region with further spectra normalization to amide I, at about 1650 cm$^{-1}$, always after a background scan collection by HATR-FTIR spectroscopy
multiple baseline correction of the 1000-1180 cm$^{-1}$ region with assignment of glucose-specific peaks at about 1030 cm$^{-1}$, 1041 cm$^{-1}$, 1118 cm$^{-1}$ and 1153 cm$^{-1}$, where the peaks at about 1030 cm$^{-1}$ and 1041 cm$^{-1}$ are always mentioned together
subject's forearm repositioning after each measured spectrum for avoidance of hydration effect
manipulating a subject's capillary blood glucose levels in order to obtain meaningful time-dependent LT's and their changes by subject himself/herself under OGTT with different doses (5 g, 20 g, 75 g), post-prandially, or under any other screening metabolic test
manipulating a subject's glucose values by HATR-FTIR such those produce meaningful time-dependent changes in the levels of CBG and in the levels of glucose values at about 1030, 1041, 1118 and 1153 cm$^{-1}$ by subject himself/herself under OGTT with different doses (5 g, 20 g, 75 g), post-prandially, or under any other screening metabolic test calculation of the LT changes between the estimated LT for the peak of CBG and the estimated LT for the peaks of each glucose value at about 1030, 1041, 1118 and 1153 cm$^{-1}$ measured by HATR-FTIR spectroscopy The invention utilizes the targeted glucose profiles by HATR-FTIR spectroscopy schematically presented in FIG. 1. "0"—point is pre-prandial, i.e. fasting, and/or before OGTT.

The CBG values and the spectral measurements furnish a data set upon which a calculation of the LT changes is made by using Equation 1, and which a calibration is also based in a qualified subject.

Equation 1 utilizes only parameters described in FIG. 1:

LT changes=LT(CBG peak level)−LT(HATR-FTIR peak level(s)(1030/1041/1080/1118/1153 cm$^{-1}$)

The various aspects of the invention are described in greater detail below.

Examples of inducing levels fluctuations/shifts in the subject's CBG values and epidermal glucose values by HATR-FTIR, in order to obtain meaningful time-dependent and dose-dependent glucose values, their LT's for maximum peaks and their LT changes towards monitored characterization of GV in a qualified subject, with or without hyperglycemia, stable or unstable, that can be used to predict the patient's risk of hyperglycemia, to stage Type II diabetes and, in general, to be considered as a new metrics of assessing the quality of metabolic control, are presented in Tables 1-5 and in FIGS. 2-6.

Subjects

Type 2 diabetes (totally 3 subjects):
Subject 1, Male, age 67, insulin therapy because of recurrent/persistent hyperglycemia, due to no response to orally prescribed tablets of Metformin for the last 7 years
Subject 2, Female, age 70, orally prescribed tablets of Metformin has been changed to a diet control
Subject 3, Male, age 69, insulin therapy because of recurrent/persistent hyperglycemia, due to no response to orally prescribed tablets of Metformin for the last 2 years
Impaired glucose tolerance, i.e. prediabetic subjects, and subjects as suspects of having impaired glucose tolerance due to occasional post-prandial hyperglycemia, based on accepted in the clinical practice interpretation of blood glucose units obtained under different conditions (mg/dL) and according to WHO Diabetes Criteria (totally 3 subjects):
Subject 1, Male, age 49, occasional post-prandial hyperglycemia
Subject 2, Male, age 58, occasional post-prandial hyperglycemia
Subject 3, Male, age 49, prediabetes
Healthy (totally 5 subjects):
Subject 1, Male, age 23
Subject 2, Male, age 24
Subject 3, Male, age 60
Subject 4, Female, age 35
Subject 5, Male, age 59

Results

1. A Formula and Method for Monitoring Individual Metabolic Response in a Qualified Subject (i) individually at each glucose value
(ii) simultaneously at all glucose values 2. A Formula and Method for Monitoring Individual Metabolic Response in a Qualified Subject (i) in one subject
(ii) between the subjects 3. A Formula and Method for Monitoring Individual Metabolic Response in a Qualified Subject (i) within one group of disease/condition
(ii) between different groups/conditions 4. A Formula and Method for Monitoring Individual Metabolic Response in a Qualified Subject (i) under one screening test
(ii) comparatively, under different screening tests 5. A Formula and Method for Monitoring Individual Metabolic Response in a Qualified Subject (i) for qualitative interpretation
(ii) for quantitative interpretation 6. A Formula and Method for Monitoring Individual Metabolic Response and for Generating Predictive Clinical Metrics in a Patient (i) for generating a pattern and parameters characterizing GV in the patients with Type 2 diabetes
(ii) for generating a pattern and parameters characterizing GV in the patients with impaired glucose tolerance, i.e. the patients with prediabetes
(iii) for generating a pattern and parameters characterizing GV in healthy subjects Tables 1-5 describe that:
the LT changes show dose-dependency in healthy, prediabetic and diabetic subjects, that differ at duration
the LT changes are the shortest in a diabetes subject and the longest in a healthy subject, independent of intaken dose of glucose under OGTT
the LT changes differ at single, bi-phasic and a cascade appearance between healthy subjects, subjects as suspects of having impaired glucose tolerance, i.e. prediabetes, and subjects with
Type 2 diabetes
the LT changes show pattern recognition for healthy subjects, prediabetic subjects and subjects with Type 2 diabetes, based on the assessed LT changes (in minutes)
the LT changes show day-to-day variations, connected to a pattern recognition FIGS. 2-11, in addition to the results, shown in Tables 1-7, show differences in GV between healthy, prediabetic and diabetic subjects towards their pattern recognition, based on specific characteristics:
recognized to healthy and prediabetic/diabetic subjects wavenumber changes, i.e. shifts of glucose-specific peaks to the left or to the right, accordingly
recognized glucose levels as low, medium and high, for healthy, prediabetic and diabetic subjects, assessed at determined time intervals under OGTT with different doses recognized meaningful time-dependent fluctuations of GV assessed at each glucose-specific value, having common and specific features for healthy, prediabetic and diabetic subjects

EXAMPLES

Example 1

FIG. 2 A-D presents differences between GV obtained between CBG values (shown by dashed lines) and each glucose value (shown by solid lines) at about 1030, 1041, 1118 and 1153 cm$^{-1}$ by HATR-FTIR spectroscopy during a 120-minute post-prandial monitoring of individual metabolic response in Subject 1 with Type 2 diabetes. The time of increment for each glucose value is indicated by a solid line along x-axis. In case of a biphasic increase, a first phase is indicated by a dashed line along x-axis.

FIG. 3 A-D presents differences between GV obtained between CBG values (shown by dashed lines) and each glucose value (shown by solid lines) at about 1030, 1041, 1118 and 1153 cm$^{-1}$ by HATR-FTIR spectroscopy during a 120-minute post-prandial monitoring of individual metabolic response in Subject 2 with Type 2 diabetes. The time of increment for each glucose value is indicated by a solid line along x-axis. In case of a biphasic increase, a first phase is indicated by a dashed line along x-axis.

FIG. 4 A-D presents differences between GV obtained between CBG values (shown by dashed lines) and each glucose value (shown by solid lines) at about 1030, 1041, 1118 and 1153 cm$^{-1}$ by HATR-FTIR spectroscopy during a 120-minute post-prandial monitoring of individual metabolic response in Subject 3 with Type 2 diabetes. The time of increment for each glucose value is indicated by a solid line along x-axis. In case of a biphasic increase, a first phase is indicated by a dashed line along x-axis.

Table 1 displays LT changes estimated within a 120-minute post-prandial monitoring of metabolic response in 3 subjects with Type 2 diabetes (S1, S2 and S3) by HATR-FTIR spectroscopy.

| Subjects | 1030-1041 cm$^{-1}$ | 1080 cm$^{-1}$ | 1118 cm$^{-1}$ | 1153 cm$^{-1}$ |
|---|---|---|---|---|
| S1 | 0' | 0' | 0' | 30' |
| S2 | 0' | 0' & 60' | 0' & 60' | 30' |
| S3 | 0' | 60' | 0' | 60' |

Example 2

Figure 5A:
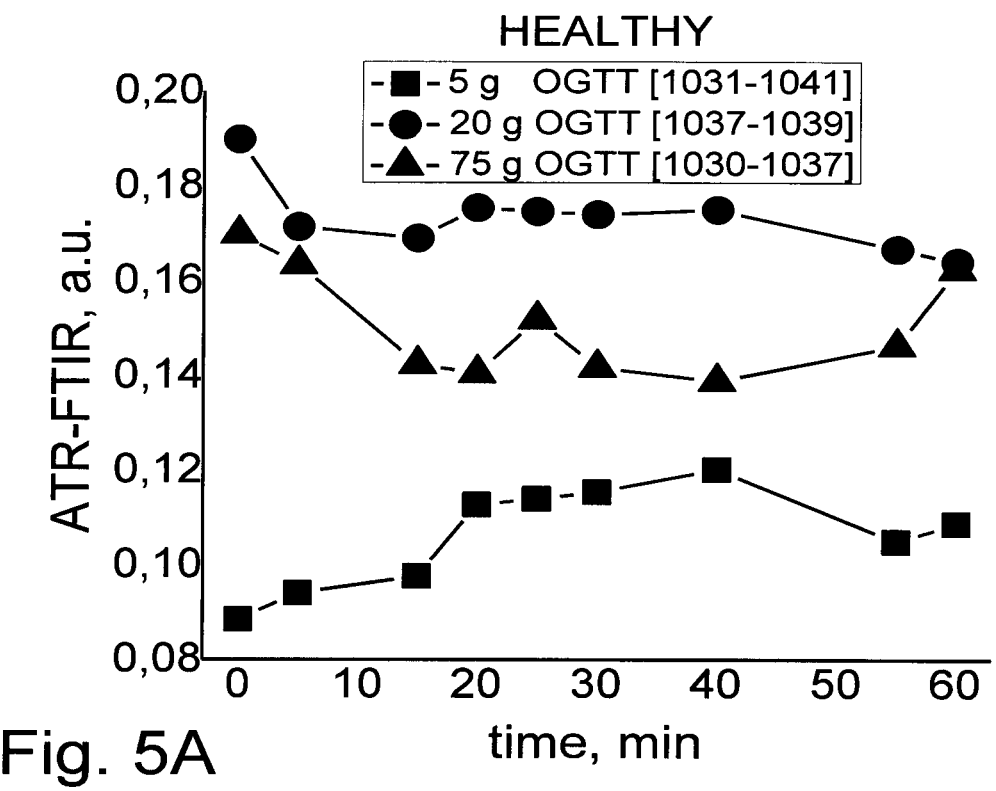
FIG. 5 A-C presents a comparative dose-dependent GV during monitoring of metabolic response by HATR-FTIR spectroscopy at about 1030, 1041, 1118 and 1153 cm$^{-1}$ during OGTT at different doses, at 5 g (low), 20 g (medium) and 75 g (high), in a healthy subject (Subject 4).
Figure 5B:
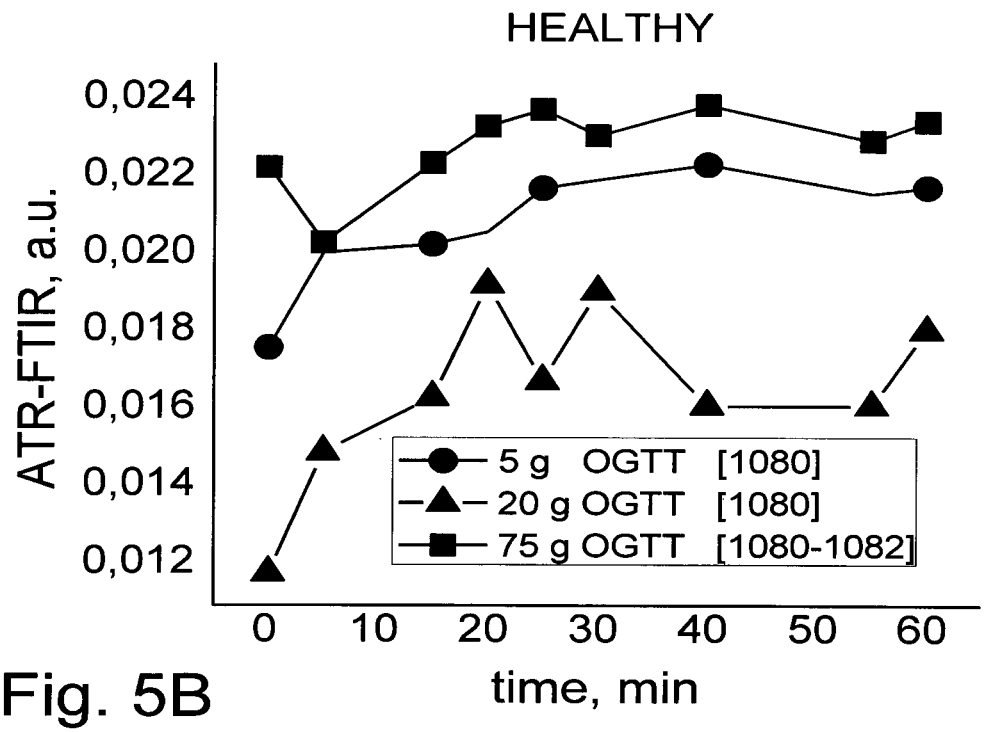
Figure 5C:
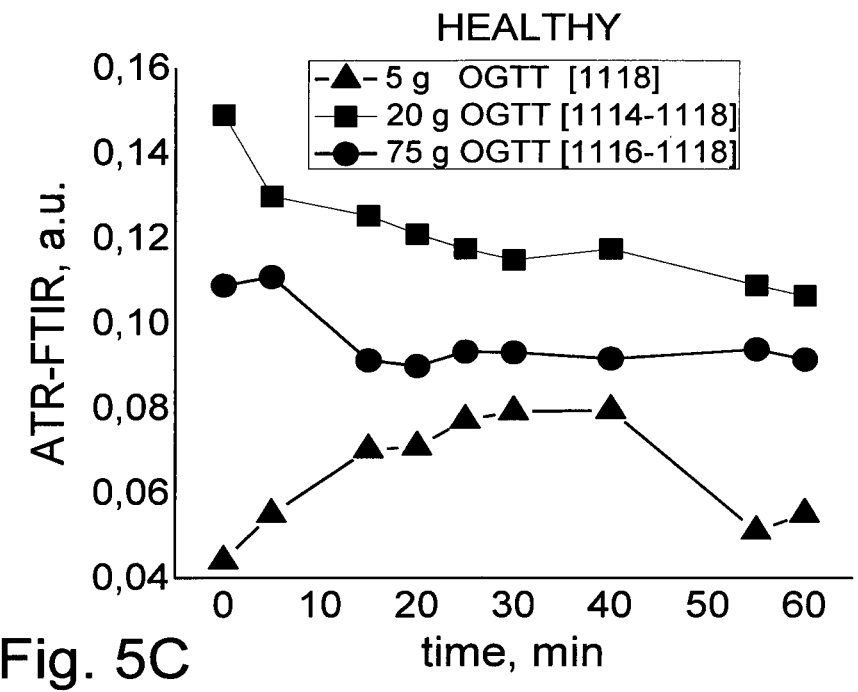

FIG. 5 A-C presents a comparative dose-dependent GV during monitoring of metabolic response by HATR-FTIR spectroscopy at about 1030, 1041, 1118 and 1153 cm$^{-1}$ during OGTT at different doses, at 5 g (low), 20 g (medium) and 75 g (high), in a healthy subject (Subject 4).

Table 2 displays LT changes between the LT for the peak of CBG and the LT peak for each measured glucose level at about 1030, 1041, 1118 and 1153 cm$^{-1}$, obtained in a healthy subject during OGTT at different doses (5 g, 20 g, 75 g).

| Healthy | LT | OGTT (5 g) | OGTT (20 g) | OGTT (75 g) |
|---|---|---|---|---|
| 1030-1041 cm$^{-1}$ | LT$_{changes}$ | 15' & 30' | 10' | 5' & 30' |
| 1080 cm$^{-1}$ | LT$_{changes}$ | 15' & 30' | 0' & 10' & 20' | 5' |
| 1118 cm$^{-1}$ | LT$_{changes}$ | 10' & 25' | 10' | 5 '& 25' |
| 1153 cm$^{-1}$ | LT$_{changes}$ | 35' & 50' | 10' & 15' | 10' |

Figure 6A:
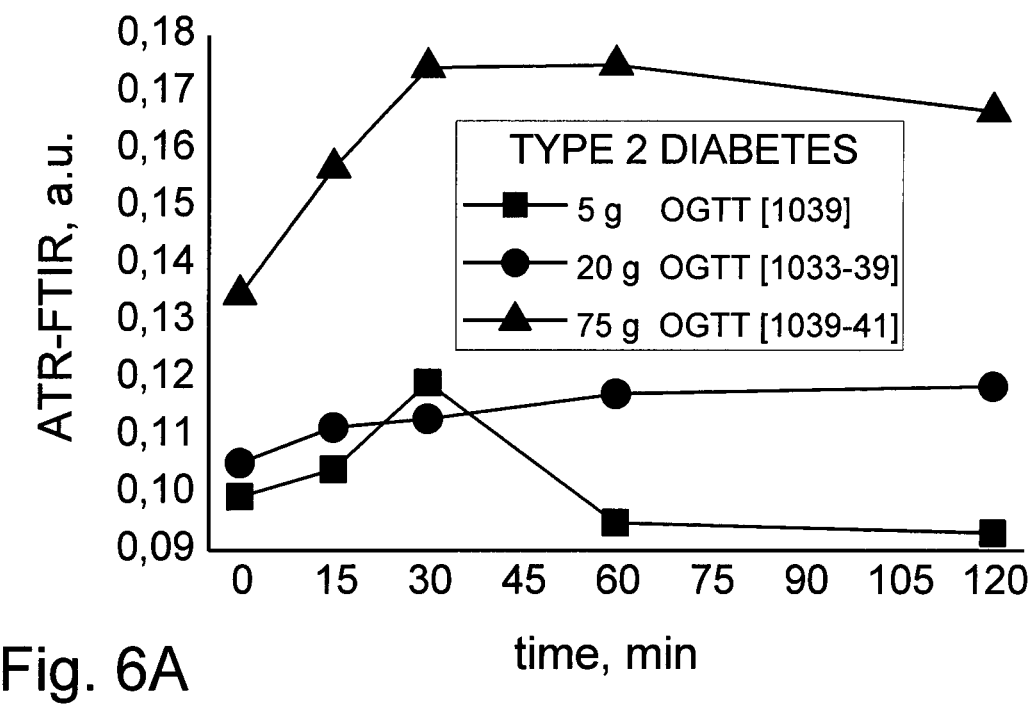
FIG. 6 A-C presents a comparative dose-dependent GV during monitoring of metabolic response by HATR-FTIR spectroscopy simultaneously shown at about 1030, 1041, 1118 and 1153 cm$^{-1}$ during OGTT at different doses, at 5 g (low), 20 g (medium) and 75 g (high), in Subject 3 with Type 2 diabetes.
Figure 6B:
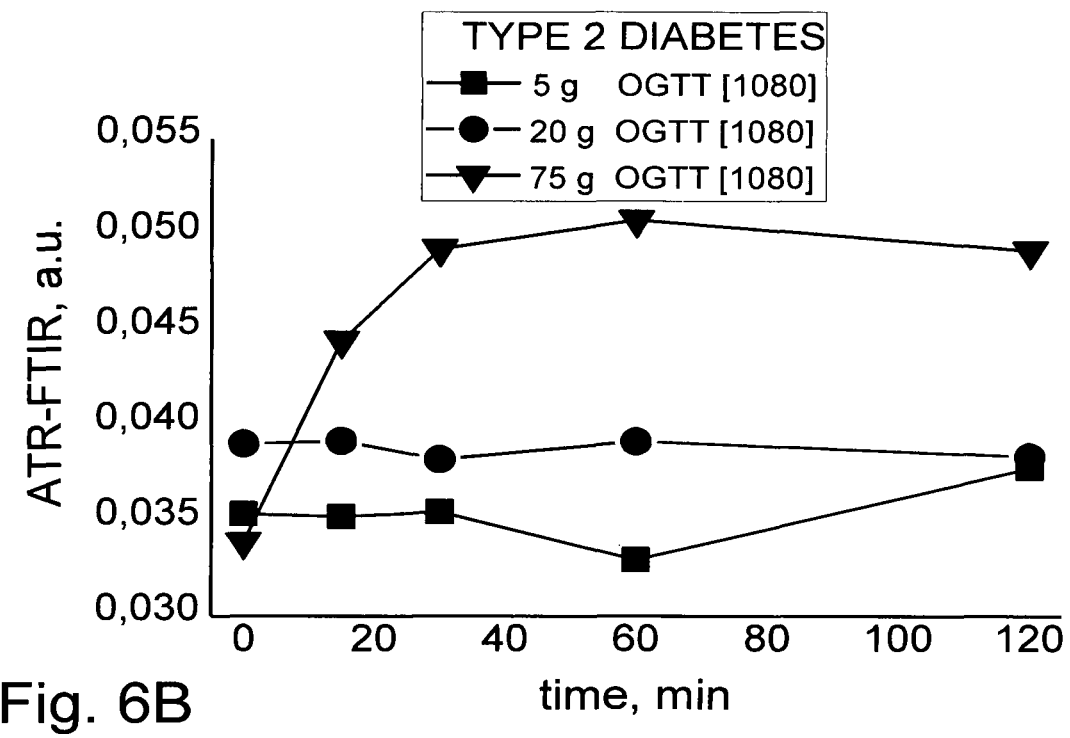
Figure 6C:
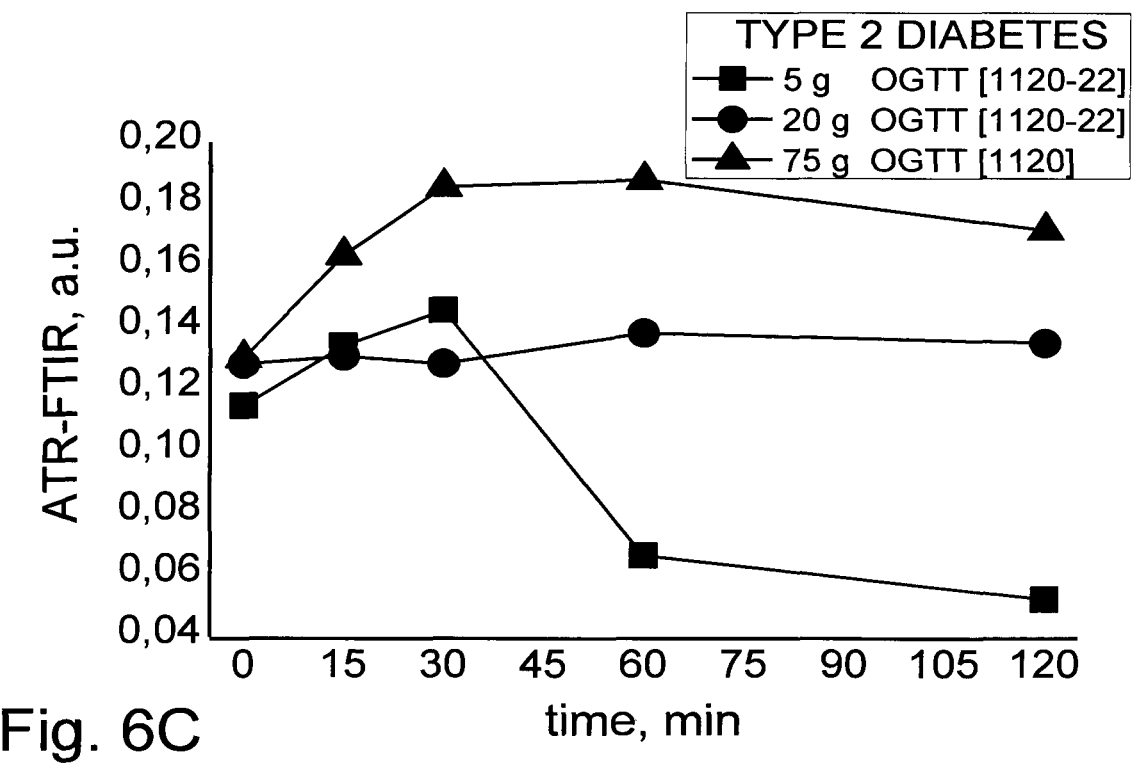

FIG. 6 A-C presents a comparative dose-dependent GV during monitoring of metabolic response by HATR-FTIR spectroscopy simultaneously shown at about 1030, 1041, 1118 and 1153 cm$^{-1}$ during OGTT at different doses, at 5 g (low), 20 g (medium) and 75 g (high), in Subject 3 with Type 2 diabetes.

Table 3 displays LT changes between the LT for the peak of CBG and the LT peak for each measured glucose level at about 1030, 1041, 1118 and 1153 cm$^{-1}$, obtained in a diabetic subject during OGTT at different doses (5 g, 20 g, 75 g).

| Type 2 diabetes | LT | OGTT (5 g) | OGTT (20 g) | OGTT (75 g) |
|---|---|---|---|---|
| 1030-1041 cm$^{-1}$ | LT$_{changes}$ | 0' & 10 | 0' | 0' |
| 1080 cm$^{-1}$ | LT$_{changes}$ | 10' | 15' | 0' |
| 1118 cm$^{-1}$ | LT$_{changes}$ | 0' & 10 & 25' | 5' | 0' |
| 1153 cm$^{-1}$ | LT$_{changes}$ | 15' & 25' | 25' & 40' | 30' |

Example 3

Figure 7A:
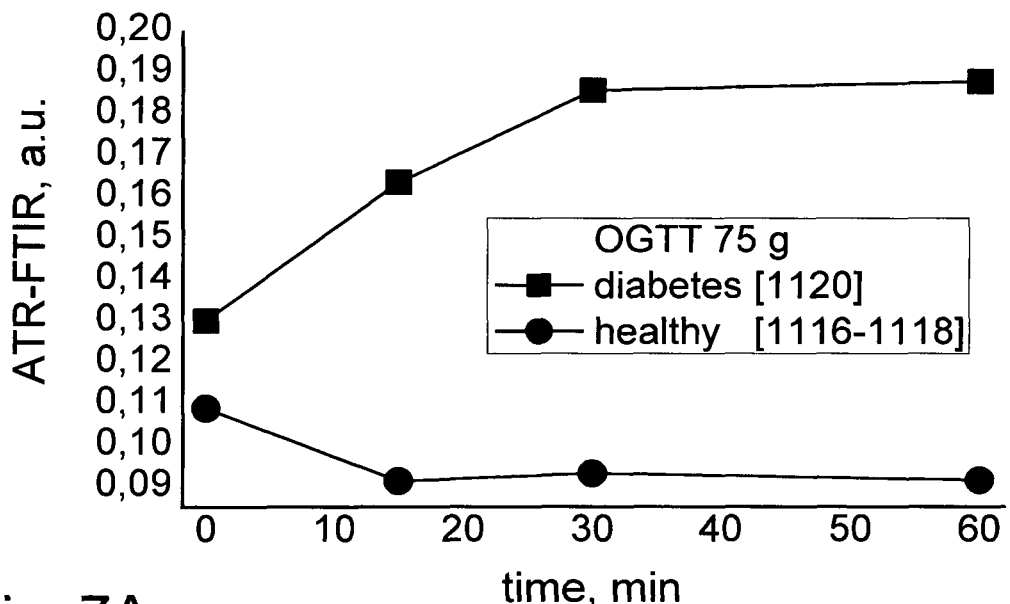
FIG. 7 A-C illustrates examples of characteristic differences in the levels of glucose values and wavenumber shifts between a healthy subject (Subject 4) and a subject with Type 2 diabetes (Subject 3) under OGTT with different doses.
Figure 7B:
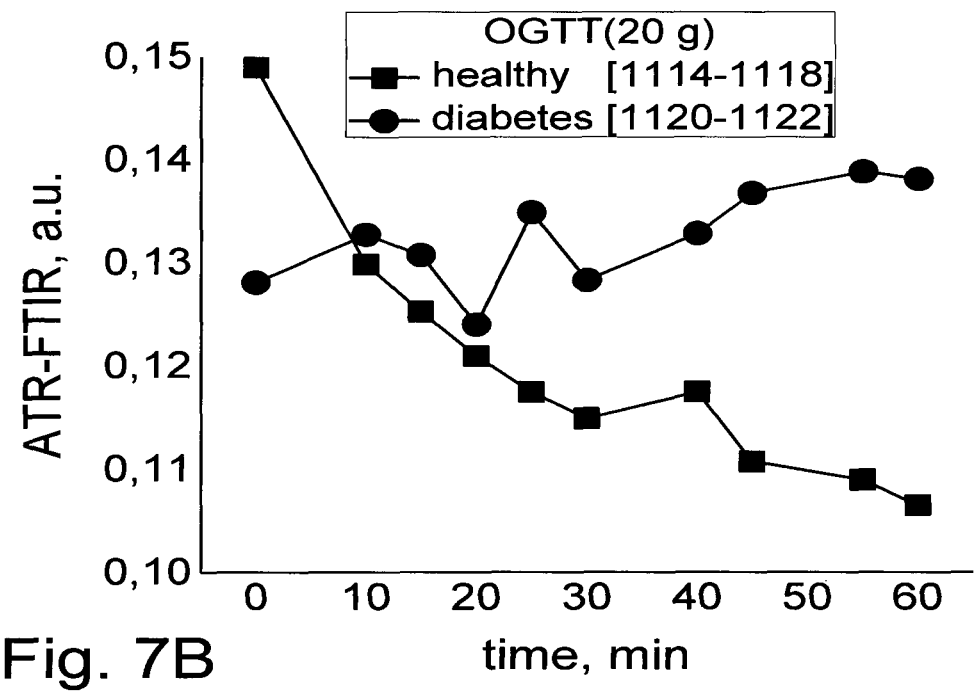
Figure 7C:
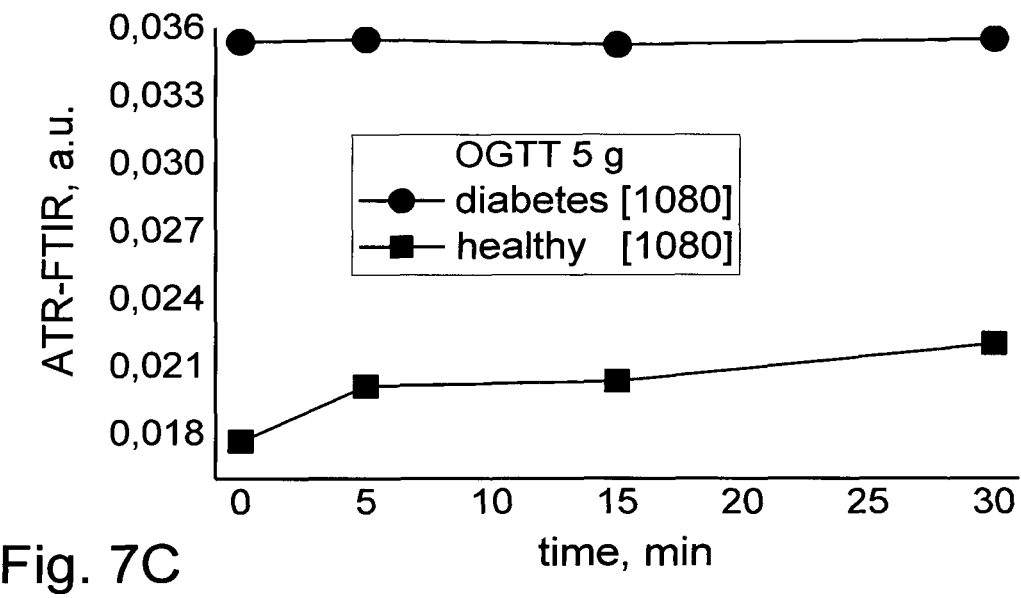
Figure 8A:
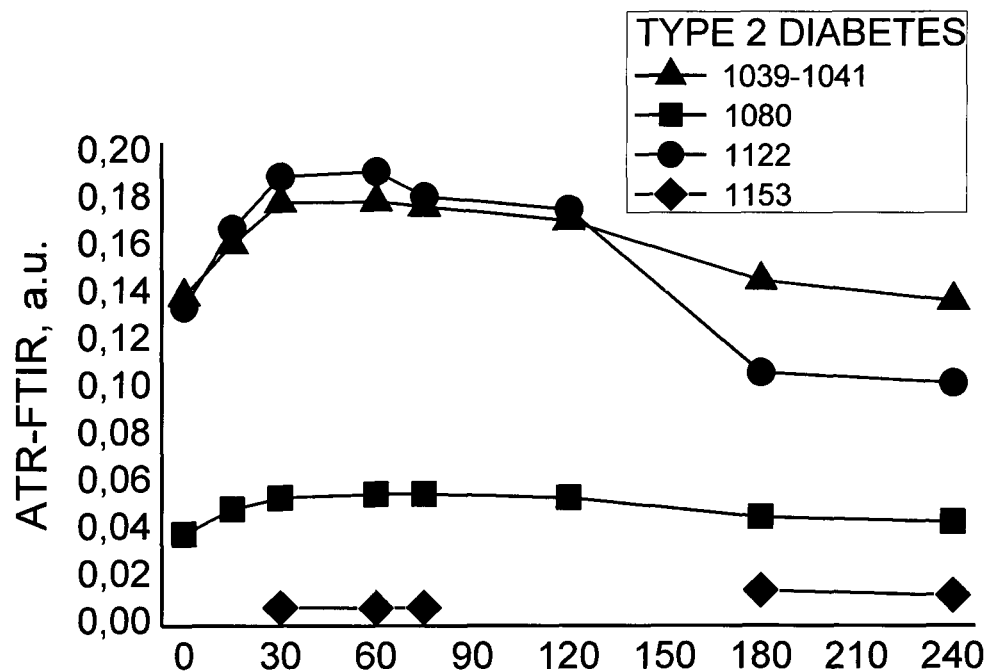
FIG. 8 A-F illustrates a variety of examples of GV simultaneously shown at about 1030, 1041, 1118 and 1153 cm$^{-1}$ by HATR-FTIR spectroscopy in 2 Type 2 diabetes (Subject 3) under OGTT with 75 g and 20 g; in a prediabetic subject (Subject 5) under OGTT with 75 g and under OGTT with 75 g in 3 healthy subjects (Subject 1, Subject 3, Subject 4).
Figure 8B:
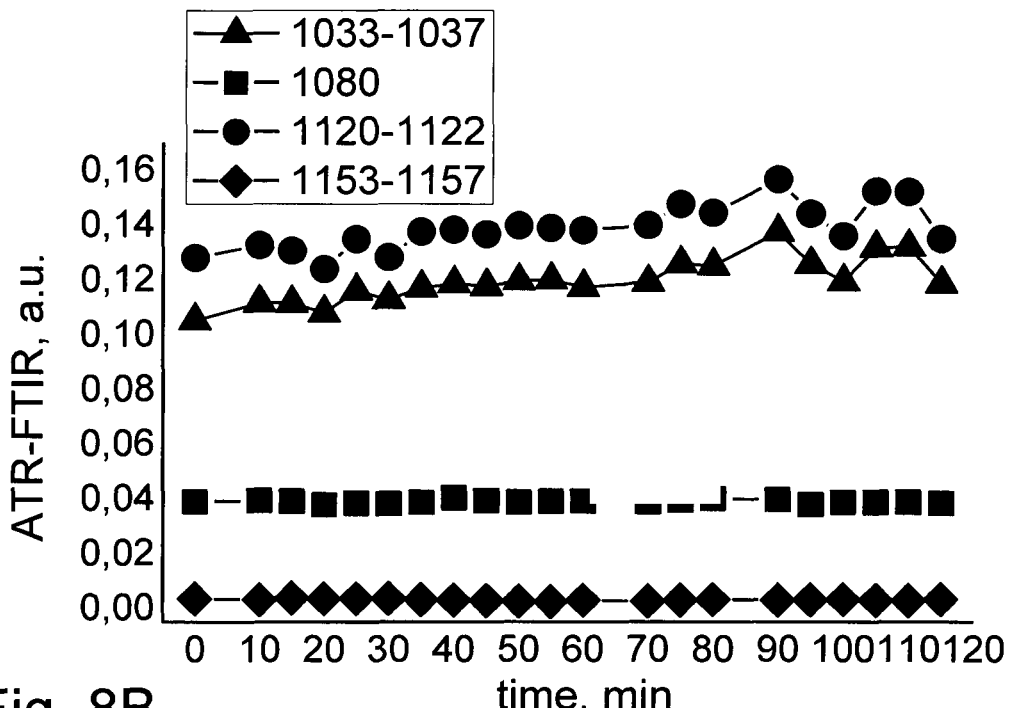
Figure 8C:
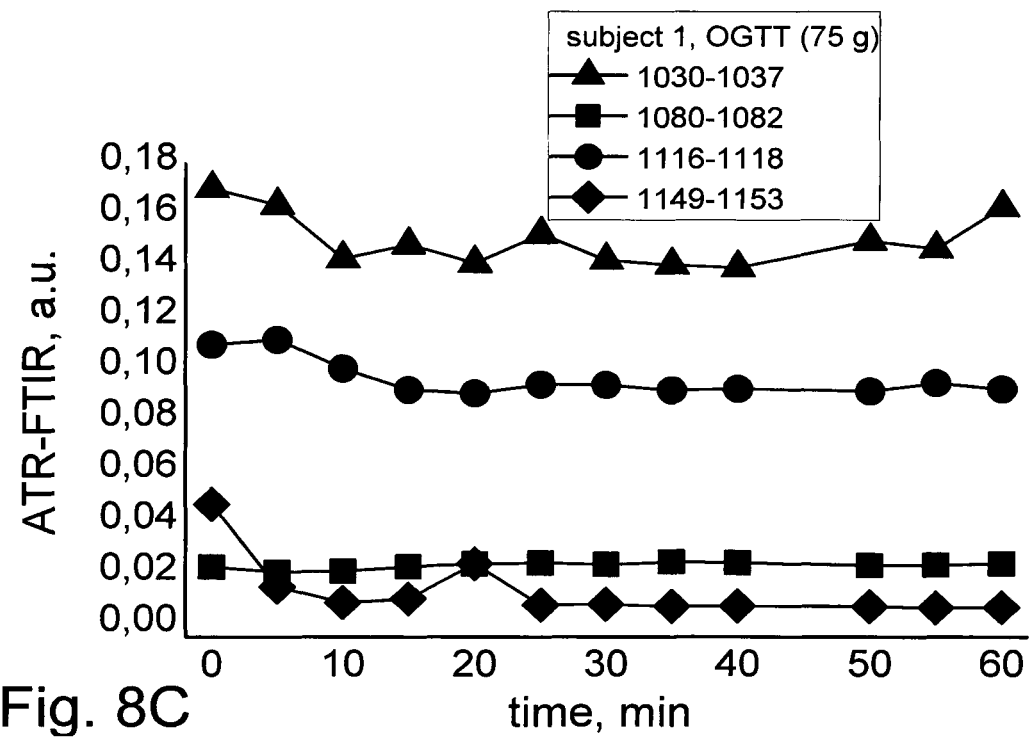
Figure 8D:
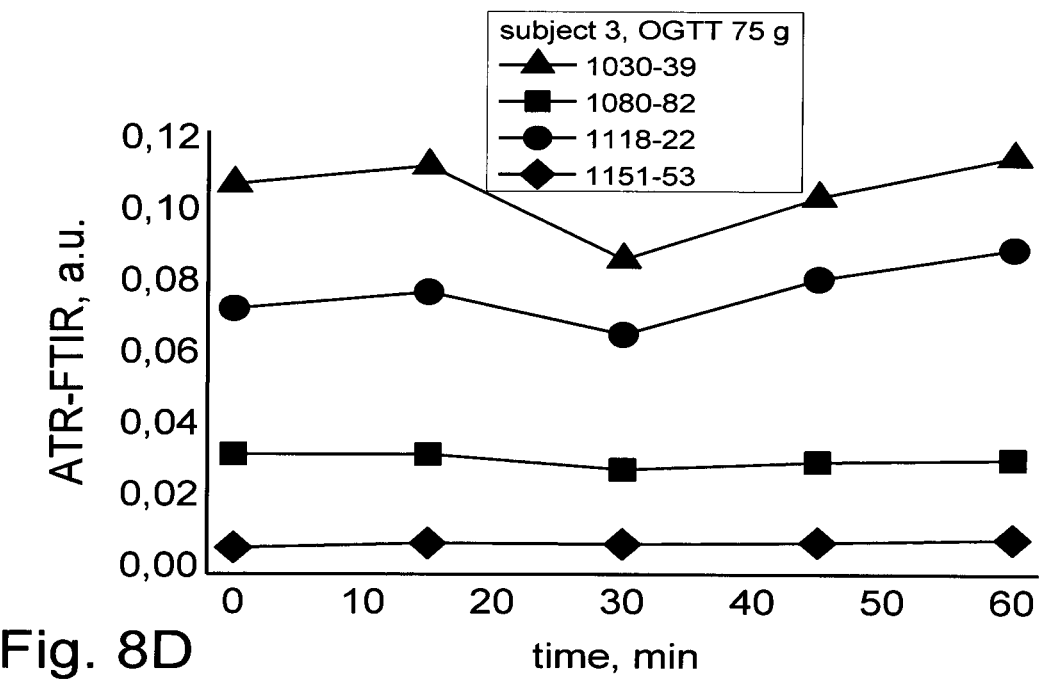
Figure 8E:
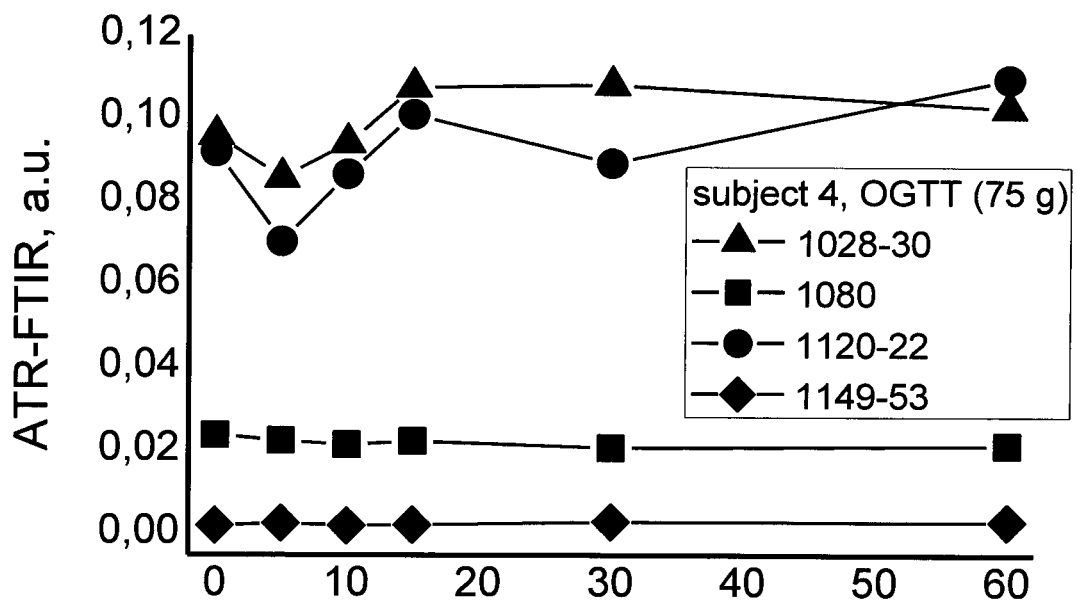
Figure 8F:
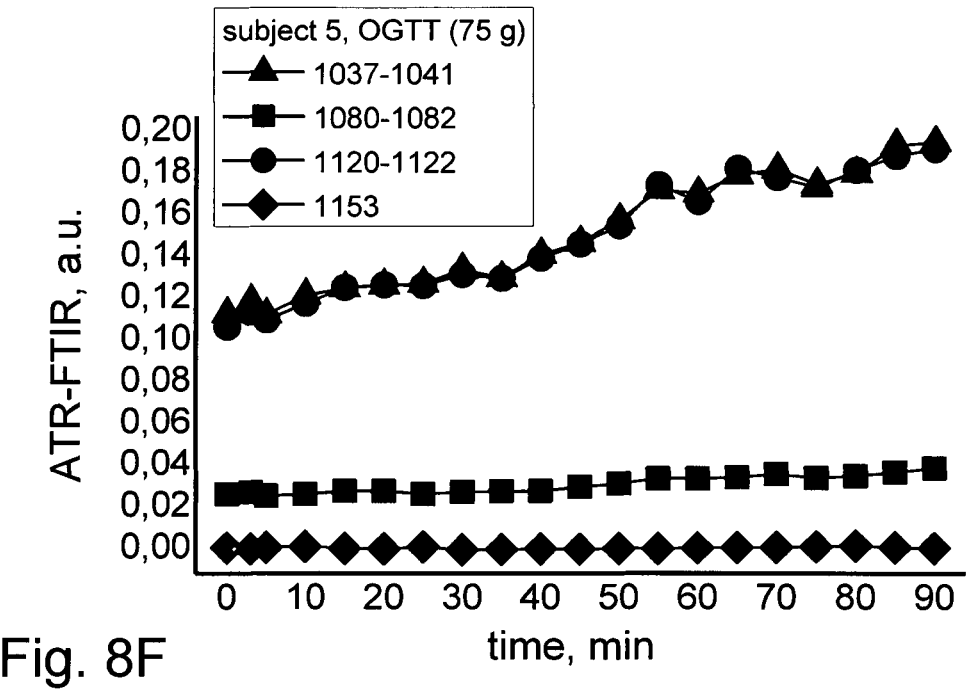
Figure 9A:
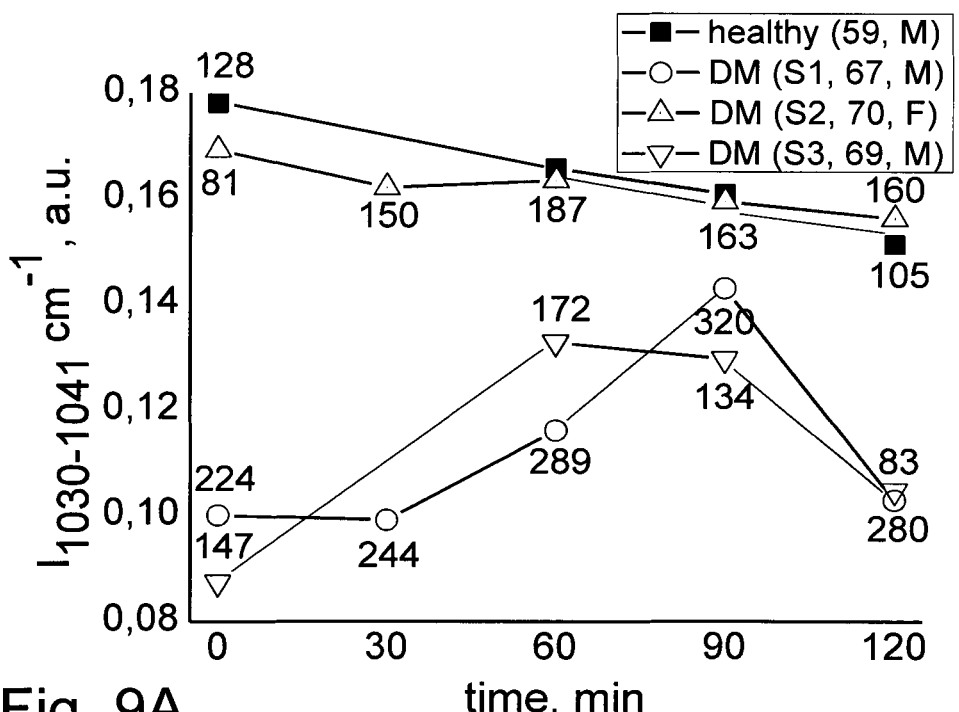
FIG. 9 A-D presents GV simultaneously shown at about 1030, 1041, 1118 and 1153 cm$^{-1}$ by HATR-FTIR spectroscopy during a 120-minute post-prandial monitoring of individual metabolic response in 3 patients (Subjects 1-3) with Type 2 diabetes, in comparison to a healthy subject (Subject 5).
Figure 9B:
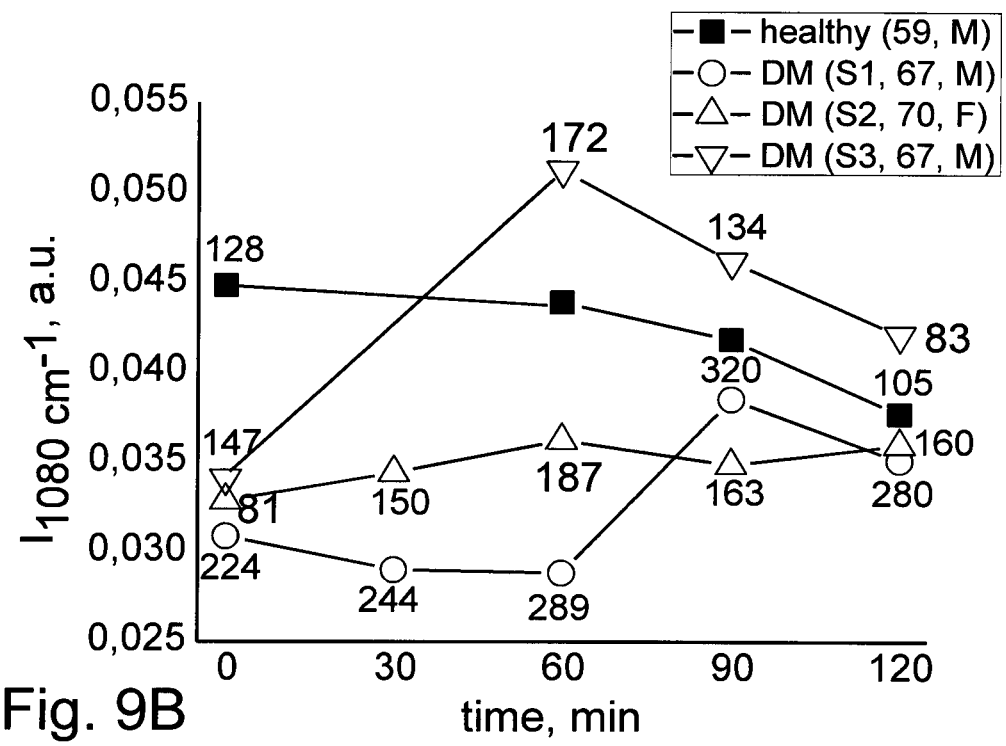
Figure 9C:
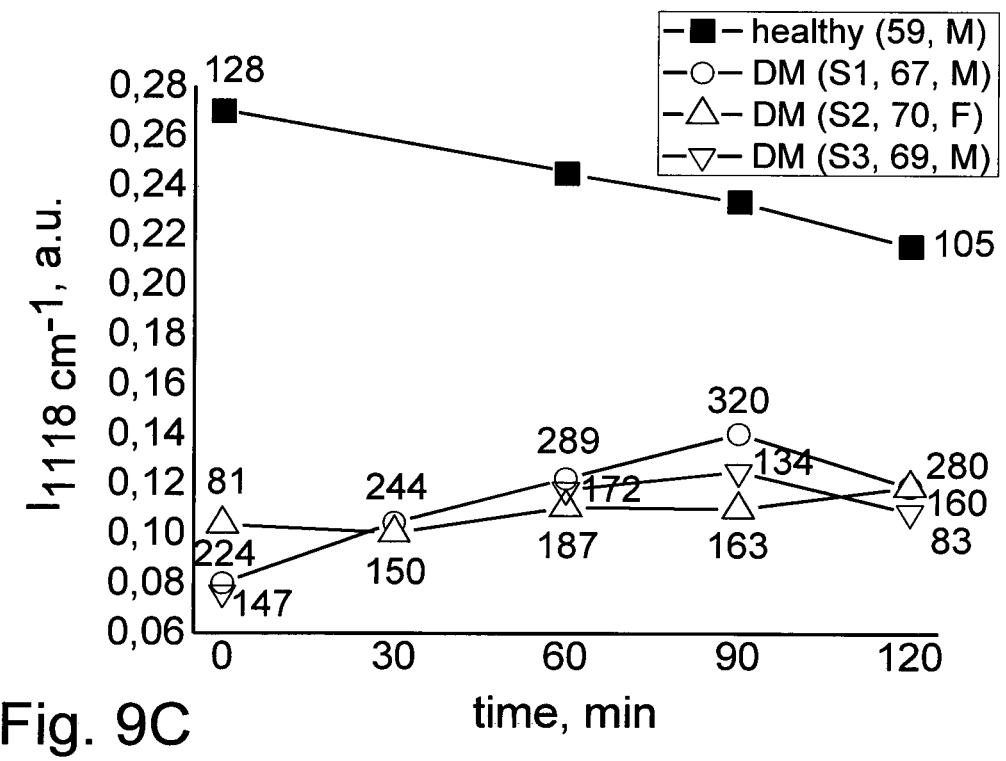
Figure 9D:
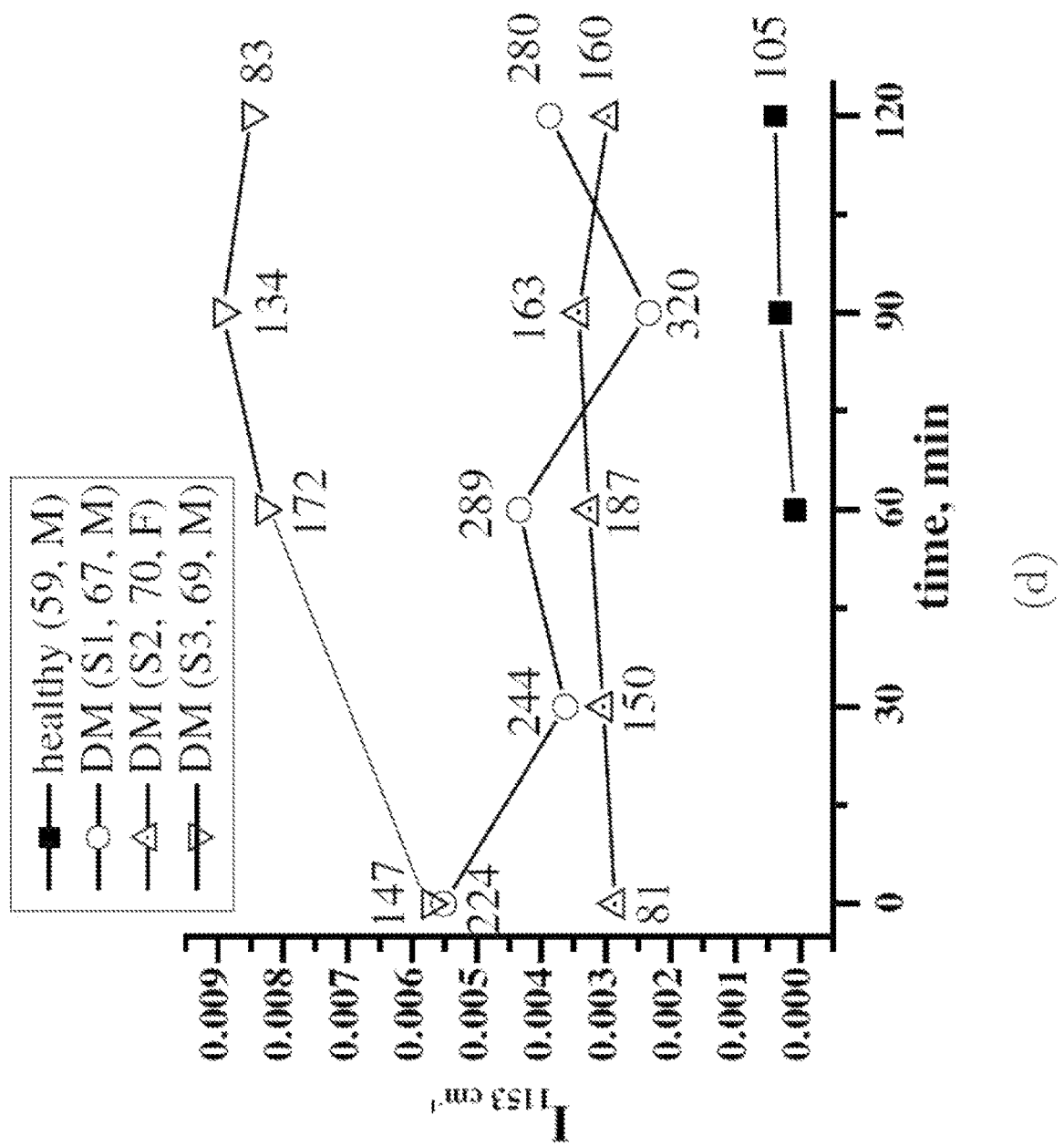

FIG. 7 A-C illustrates examples of characteristic differences in the levels of glucose values and wavenumber shifts between a healthy subject (Subject 4) and a subject with Type 2 diabetes (Subject 3) under OGTT with different doses.

Table 4 displays LT changes under OGTT with 75 g., i.e. clinical, a healthy subject vs. a subject with Type 2 diabetes.

| Subjects | healthy | Type 2 diabetes |
|---|---|---|
| 1030-1041 cm$^{-1}$ | 15' & 30' | 10' |
| 1080 cm$^{-1}$ | 15' & 30' | 10' |
| 1118 cm$^{-1}$ | 10' & 25' | 0' & 10' & 25' |
| 1153 cm$^{-1}$ | 35' & 50' | 15' & 25' |

Table 5 displays LT changes under OGTT with 20 g., a healthy subject vs. a subject with Type 2 diabetes.

| Subjects | healthy | Type 2 diabetes |
|---|---|---|
| 1030-1041 cm$^{-1}$ | 10' | 0' |
| 1080 cm$^{-1}$ | 0' & 10' & 20' | 15' |
| 1118 cm$^{-1}$ | 10' | 5' |
| 1153 cm$^{-1}$ | 10' & 15' | 25' & 40' |

Example 4

FIG. 8 A-F illustrates a variety of examples of GV simultaneously shown at about 1030, 1041, 1118 and 1153 cm$^{-1}$ by HATR-FTIR spectroscopy in 2 Type 2 diabetes (Subject 3) under OGTT with 75 g and 20 g; in a prediabetic subject (Subject 5) under OGTT with 75 g and under OGTT with 75 g in 3 healthy subjects (Subject 1, Subject 3, Subject 4).

Example 5

FIG. 9 A-D presents GV simultaneously shown at about 1030, 1041, 1118 and 1153 cm$^{-1}$ by HATR-FTIR spectroscopy during a 120-minute post-prandial monitoring of individual metabolic response in 3 patients (Subjects 1-3) with Type 2 diabetes, in comparison to a healthy subject (Subject 5). A 120-minute post-prandial monitoring of metabolic response in 3 subjects (S1, S2, and S3) with Type 2 DM and 1 healthy control subject ("0"-point is pre-prandial). CBG levels in mg/dL are shown in numbers along curves for each measured subject.

Example 6

Figure 10A:
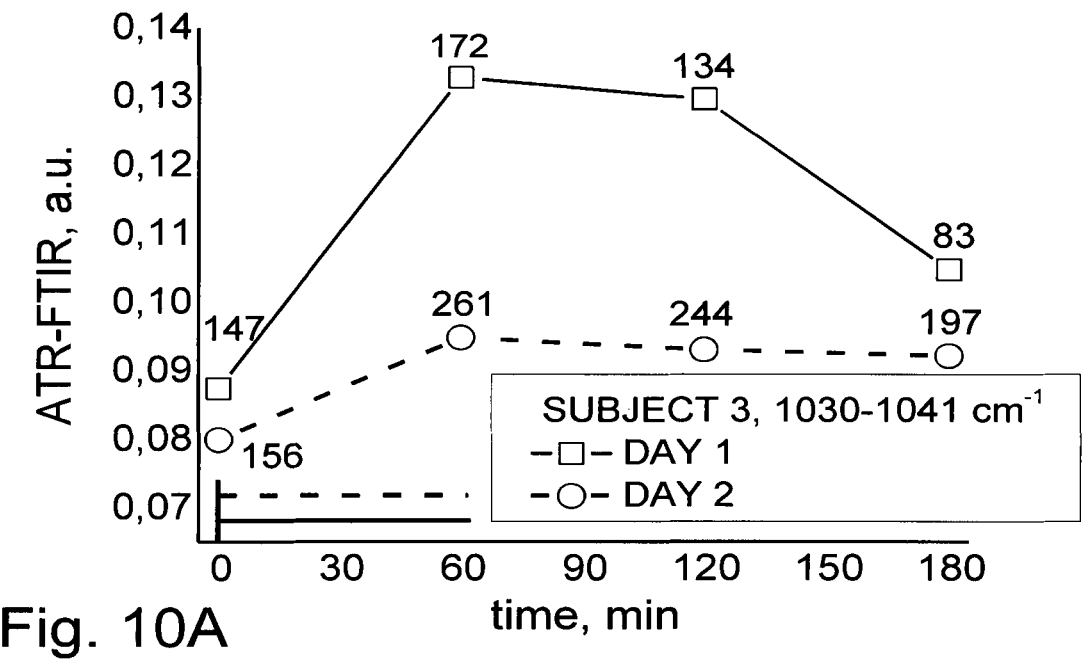
FIG. 10 A-C presents day-to-day variations on GV during a 120-minute post-prandial monitoring of individual metabolic response in Subject 3 with Type 2 diabetes on 2 consecutive days, comparatively shown at about 1030, 1041, 1080 and 1118 cm$^{-1}$ by HATR-FTIR spectroscopy.
Figure 10B:
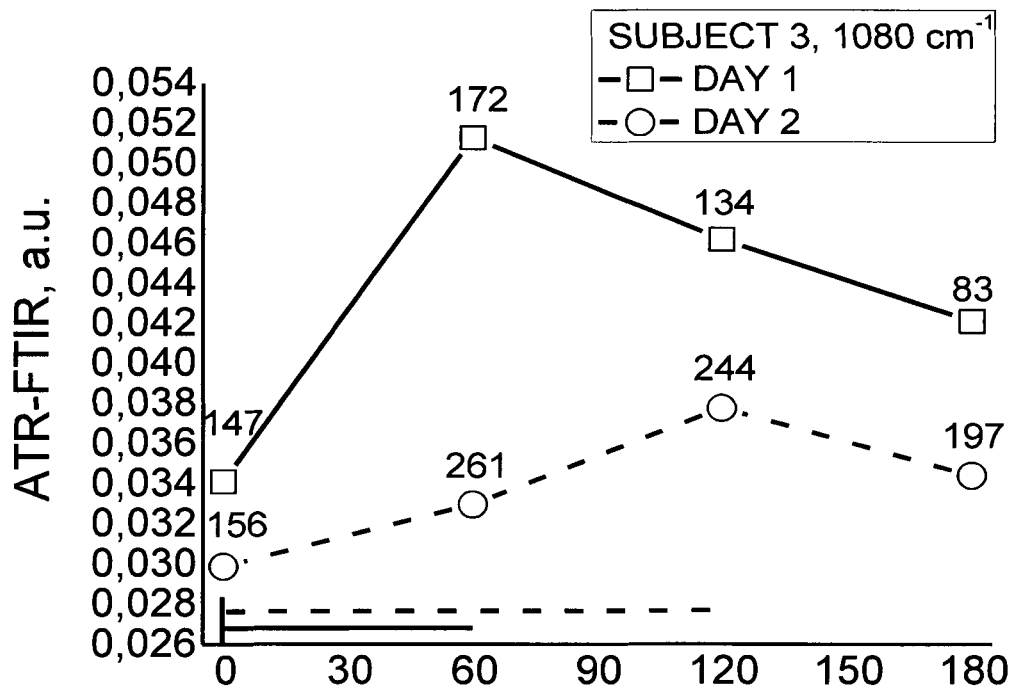
Figure 10C:
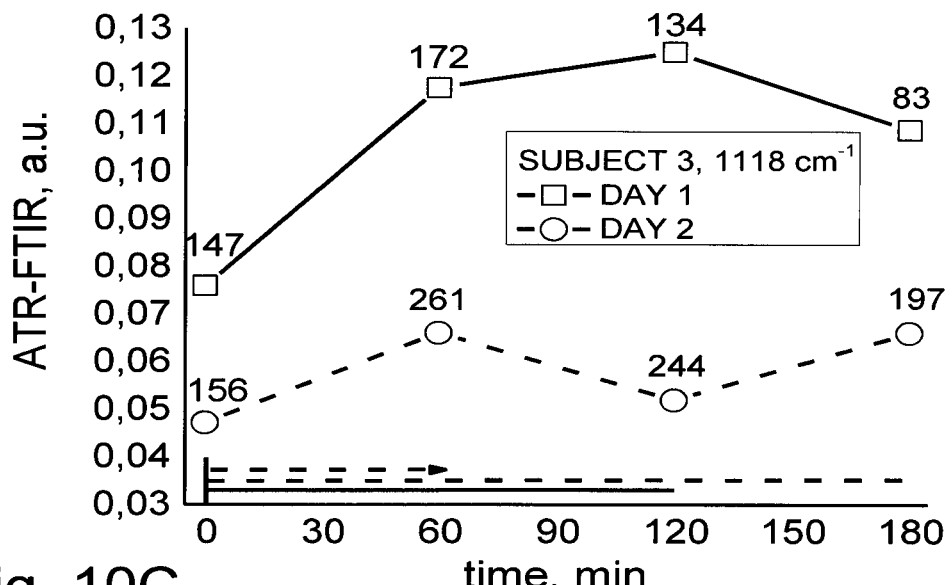
Figure 11A:
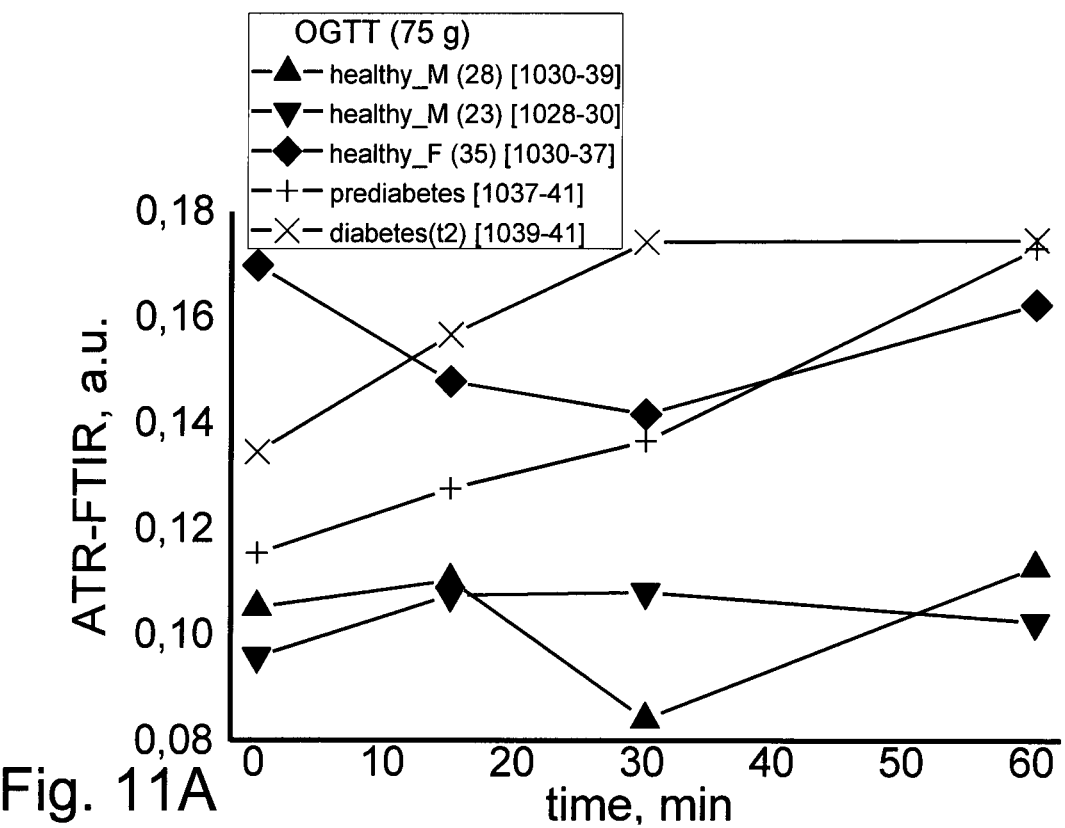
FIG. 11 A-D comparatively presents GV during monitoring of individual metabolic response in 3 healthy subjects (Subjects 1, 2, 4), in 1 subject as a suspect of having impaired glucose tolerance, i.e. prediabetes (Subject 3), and in Subject 3 with Type 2 diabetes by HATR-FTIR spectroscopy.
Figure 11B:
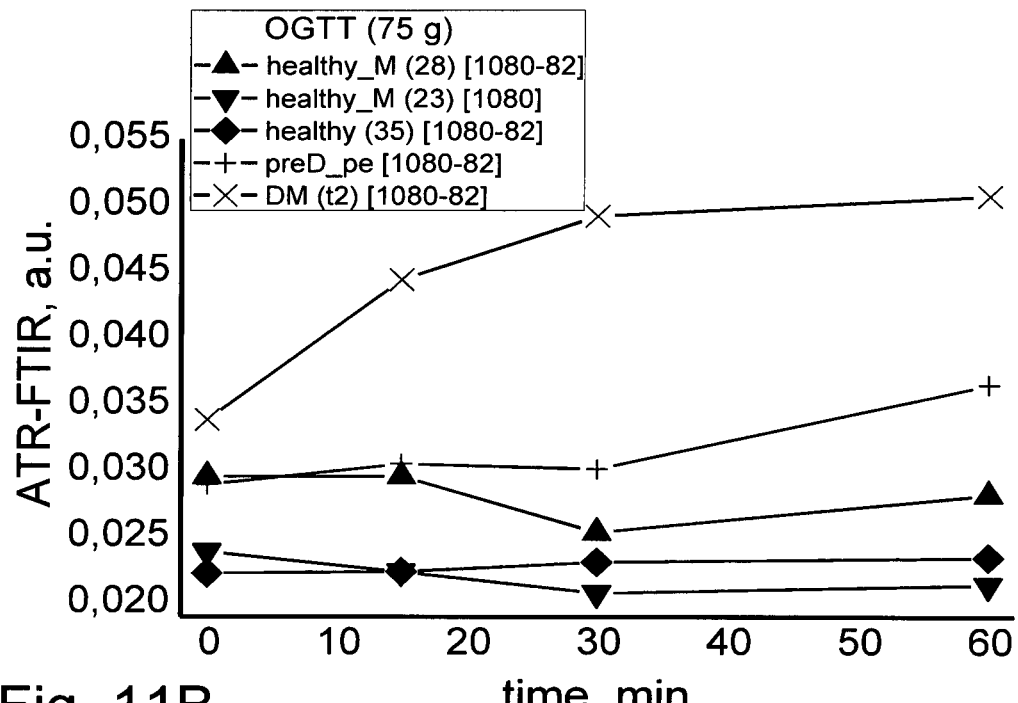
Figure 11C:
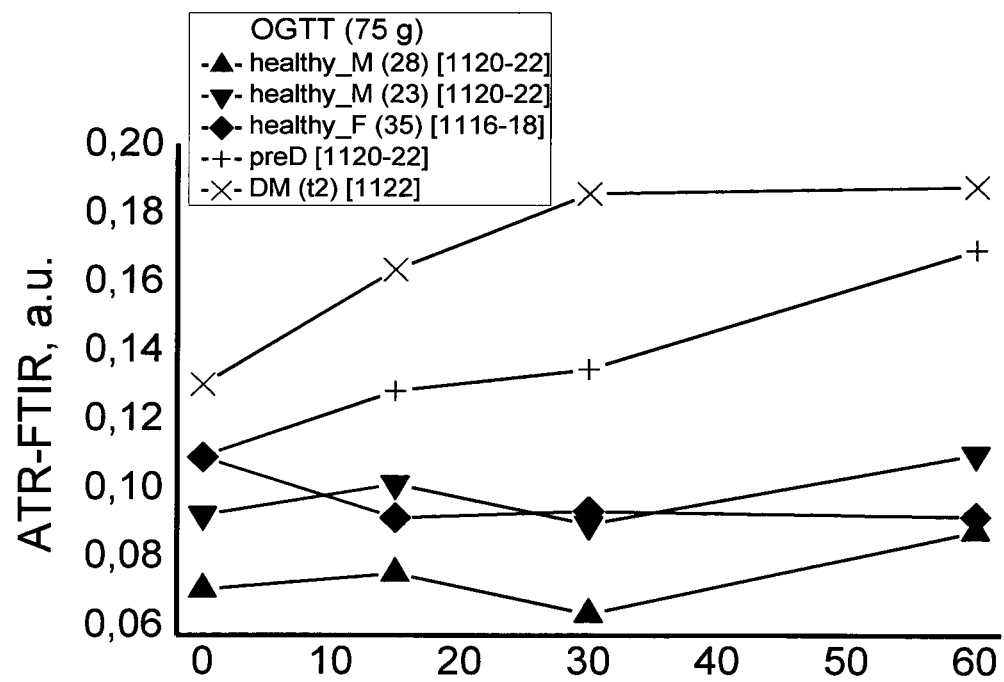
Figure 11D:
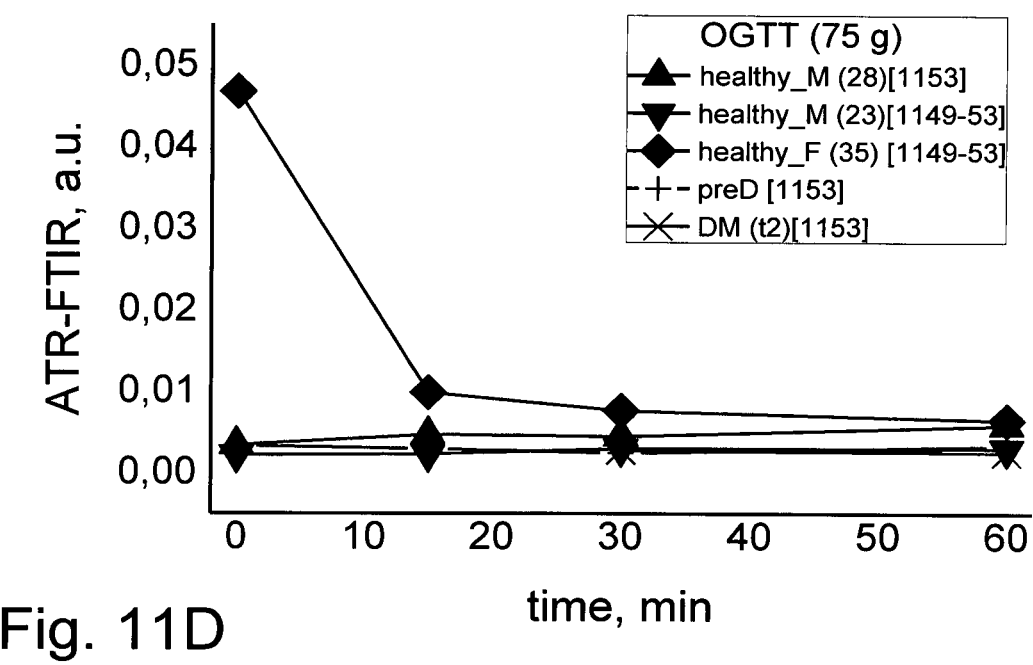

FIG. 10 A-C presents day-to-day variations on GV during a 120-minute post-prandial monitoring of individual metabolic response in Subject 3 with Type 2 diabetes on 2 consecutive days, comparatively shown at about 1030, 1041, 1080 and 1118 cm$^{-1}$ by HATR-FTIR spectroscopy.

Table 6 displays LT changes estimated for the same subject with Type 2 diabetes on 2 consecutive days.

| Subjects | 1030-1041 cm$^{-1}$ | 1080 cm$^{-1}$ | 1118 cm$^{-1}$ | 1153 cm$^{-1}$ |
| --- | --- | --- | --- | --- |
| S3 (Day 1) | 0' | 60' | 0' | 60' |
| S3 (Day 2) | 0' | | 60' | — |

Example 7

FIG. 11 A-D comparatively presents GV during monitoring of individual metabolic response in 3 healthy subjects (Subjects 1, 2, 4), in 1 subject as a suspect of having impaired glucose tolerance, i.e. prediabetes (Subject 3), and in Subject 3 with Type 2 diabetes by HATR-FTIR spectroscopy.

Table 7 displays OGTT (75 g), i.e. clinical OGTT, demonstrate estimated LT changes for healthy, prediabetic and diabetic subjects.

| Subjects | healthy | prediabetes | Type 2 diabetes |
| --- | --- | --- | --- |
| 1030-1041 cm$^{-1}$ | 5' & 30' | 5' & 20' & 30' & 45' | 0' |
| 1080 cm$^{-1}$ | 5' | 5' & 20' & 45' | 0' |
| 1118 cm$^{-1}$ | 5' & 25' | 5' & 20' & 30' & 40' | 0' |
| 1153 cm$^{-1}$ | 10' | 0' & 15' & 25' & 55' | 30' |

The invention claimed is:

1. A method of patterned data analysis for monitoring individual metabolic response and for generating predictive clinical metrics on HATR-FTIR spectroscopy by determining spectral characteristics of glucemic variability for healthy, prediabetic, and diabetic subjects, comprising of:

(i) assigning glucose-specific peaks with characteristic absorption wave numbers at 1030 cm$^{-1}$, 1041 cm$^{-1}$, 1080 cm$^{-1}$, 1118 cm$^{-1}$, and 1153 cm$^{-1}$ in the 700-4000 cm$^{-1}$ region in gathered HATR-FTR spectra from the forearm of a tested subject under post-prandial glucose test or oral glucose tolerance test with different doses at 5 g, 20 g, and 75 g, wherein oral glucose tolerance test is abbreviated OGTT, wherein spectrally assigned glucose-specific peaks at 1030 cm$^{-1}$ and 1041 cm$^{-1}$ are always bounded together bands;

(ii) determining spectral characteristics of glucemic variability for each assigned glucose-specific peak in correlation with the peak position and its shift to the left or to the right in HATR-FTIR spectra, wherein glucemic variability is abbreviated GV, wherein shifts of the peak position at 1030-1041 cm$^{-1}$, 1118 cm$^{-1}$, and 1153 cm$^{-1}$ are characteristic for healthy, prediabetic, and diabetic subjects under post-prandial glucose test or OGTT with different doses at 5 g, 20 g, and 75 g;

(iii) determining spectral characteristics of GV for each assigned glucose-specific peak in correlation with the peak level in HATR-FTIR spectra, wherein determination of the highest peak level at 1030-1041 cm$^{-1}$ and determination of the highest peak level among all assigned glucose-specific peaks is characteristic for healthy, prediabetic, and diabetic subjects under post-prandial glucose test or OGTT with different doses at 5 g, 20 g, and 75 g;

(iv) determining spectral characteristics of GV for each assigned glucose-specific peak in correlation with dose-dependent dynamic changes of the peak level under a continuous 120-minute test monitoring at predetermined time-intervals from the starting till the ending time-points under comparative OGTT test with 5 g, 20 g, and 75 g glucose, wherein the levels of the peaks at 1030-1041 cm$^{-1}$, 1080 cm$^{-1}$, 1118 cm$^{-1}$, and 1153 cm$^{-1}$ are independent to intaken dose of glucose under OGTT at 5 g, 20 g, and 75 g in healthy subjects, and wherein levels of the peaks at 1030-1041 cm$^{-1}$, 1080 cm$^{-1}$, 1118 cm$^{-1}$, and 1153 cm$^{-1}$ are dependent to intaken dose of glucose under OGTT at 5 g, 20 g, and 75 g in prediabetic and diabetic subjects; and (v) recognizing the spectral pattern of individual metabolic response by a continuous monitoring of GV, to be specific for healthy, prediabetic, and diabetic subjects, wherein the spectral pattern with predominant left-shifted mean peak position towards 1030 cm$^{-1}$ at 1030-1041 cm$^{-1}$, predominant left-shifted mean peak position towards 1116-1118 cm$^{-1}$ at 1118 cm$^{-1}$, predominant left-shifted mean peak position towards 1149-1153 cm$^{-1}$ at 1153 cm$^{-1}$, highest glucose peak levels at 1030-1041 cm$^{-1}$ over for peaks levels at 1080 cm$^{-1}$, 1118 cm$^{-1}$, and 1153 cm$^{-1}$, lowest glucose peak levels at 1153 cm$^{-1}$ below peaks levels at 1030-1041 cm$^{-1}$, 1080 cm$^{-1}$, and 1118 cm$^{-1}$, independent to intaken glucose dose peak levels at 1030-1041 cm$^{-1}$, 1080 cm$^{-1}$, 1118 cm$^{-1}$, and 1153 cm$^{-1}$ under OGTT at 5 g, 20 g, and 75 g, wherein the dose at 5 g is low, the dose at 20 g is medium, and the dose at 75 g is high, to be specific for a healthy subject, the spectral pattern with predominant right-shifted mean peak position towards 1037-1041 cm$^{-1}$ at 1030-1041 cm$^{-1}$, predominant right-shifted mean peak position towards 1120-1122 cm$^{-1}$ at 1118 cm$^{-1}$ similarly high peak levels at 1030-1041 cm$^{-1}$, and at 1118 cm$^{-1}$ over for peak levels at 1080 cm$^{-1}$ and 1153 cm$^{-1}$, lowest glucose peak levels at 1153 cm$^{-1}$ below peaks levels at 1030-1041 cm$^{-1}$, 1080 cm$^{-1}$, and 1118 cm$^{-1}$, dependent to intaken glucose dose peak levels at 1030-1041 cm$^{-1}$, 1080 cm$^{-1}$, and 1118 cm$^{-1}$ under OGTT at 5 g, 20 g, and 75 g, to be specific for a prediabetic subject, and the spectral pattern with dominant right-shifted mean peak position towards 1041 cm$^{-1}$ at 1030-1041 cm$^{-1}$, dominant right-shifted mean peak position towards 1120-1122 cm$^{-1}$ at 1118 cm$^{-1}$, dominant right-shifted mean peak position towards 1153-1157 $cm^{-1}$ at 1153 $cm^{-1}$, highest glucose peak levels at 1118 $cm^{-1}$ over for peak levels at 1030-1041 $cm^{-1}$ 1080 $cm^{-1}$, and 1153 $cm^{-1}$, lowest glucose peak levels at 1153 $cm^{-1}$ below peaks levels at 1030-1041 $cm^{-1}$, 1080 $cm^{-1}$, and 1118 $cm^{-1}$, dependent to intaken glucose dose peak levels at 1030-1041 $cm^{-1}$, 1080 $cm^{-1}$, and 1118 $cm^{-1}$ under OGTT at 5 g, 20 g, and 75 g, to be specific for a diabetic subject with type 2.

2. A method of patterned data analysis for monitoring individual metabolic response and for generating predictive clinical metrics on HATR-FTIR spectroscopy by determining spectral characteristics of the latency time for healthy, prediabetic, and diabetic subjects, comprising of:

(i) assigning glucose-specific peaks with characteristic absorption wave numbers at 1030 $cm^{-1}$, 1041 $cm^{-1}$, 1080 $cm^{-1}$, 1118 $cm^{-1}$, and 1153 $cm^{-1}$ in the 700-4000 $cm^{-1}$ region in gathered HATR-FTIR spectra from the forearm of a tested subject under post-prandial glucose test or OGTT with different doses at 5 g, 20 g, and 75 g, wherein spectrally assigned glucose-specific peaks at 1030 $cm^{-1}$ and 1041 $cm^{-1}$ are always bounded together bands;

(ii) calculating the latency time duration for each assigned glucose-specific peak at 1030-1041 $cm^{-1}$, 1080 $cm^{-1}$, 1118 $cm^{-1}$, and 1153 $cm^{-1}$, wherein latency time is abbreviated LT, wherein the LT is the time interval from the time-point of induction of glucose excursions till the time-point of maximum detected levels of the glucose-specific peaks at 1030-1041 $cm^{-1}$, 1080 $cm^{-1}$, 1118 $cm^{-1}$, and 1153 $cm^{-1}$ on HATR-FTIR spectrometer in the interstitial fluid of skin tissue;

(iii) comparing calculated LT duration for each assigned glucose-specific peak at 1030-1041 $cm^{-1}$, 1080 $cm^{-1}$, 1118 $cm^{-1}$, and 1153 $cm^{-1}$ in the interstitial fluid of skin tissue with the LT duration in capillary blood glucose gathered in the subject by calculating the LT differences, wherein capillary blood glucose is abbreviated CBG, wherein the LT is the time interval from the time-point of induction of glucose excursions till the time-point of maximum detected levels of the CBG measurements in the subject in capillary blood glucose;

(iv) determining spectral characteristics for calculated LT and LT difference intervals for each assigned glucose-specific peak in correlation with their durations, wherein the shortest and the longest intervals in minutes to be specific for healthy, prediabetic, and diabetic subjects;

(v) determining spectral characteristics for calculated LT and LT difference intervals for each assigned glucose-specific peak in correlation with their phasic appearances, wherein single, bi-phasic, and cascading multi-phase appearance to be specific for healthy, prediabetic, and diabetic subjects;

(vi) determining spectral characteristics for calculated LT and LT difference intervals for each assigned glucose-specific peak in correlation with dose-dependency, to be specific for healthy, prediabetic, and diabetic subjects; and (vii) determining the spectral pattern of individual metabolic response by calculating LT and LT difference intervals for each assigned glucose-specific peak under post-prandial glucose test and OGTT with different doses at 5 g, 20 g, and 75 g, to be specific for healthy, prediabetic, and diabetic subjects, wherein the spectral pattern characterized by bi-phase LTs and LT differences at 1030-1041 $cm^{-1}$ of 15 min and 30 min under OGTT at 5 g, single-phase LTs and LT differences at 1030-1041 $cm^{-1}$ of 10 min under OGTT at 20 g, bi-phase LTs and LT differences at 1030-1041 $cm^{-1}$ of 5 min and 30 min under OGTT at 75 g, bi-phase LTs and LT differences at 1080 $cm^{-1}$ of 15 min and 30 min under OGTT at 5 g, cascading multi-phase LTs and LT differences at 1080 $cm^{-1}$ of 0 min, 10 min, and 20 min under OGTT at 20 g, single-phase LTs and LT differences at 1080 $cm^{-1}$ of 5 min under OGTT at 75 g, bi-phase LTs and LT differences at 1118 $cm^{-1}$ s of 10 min and 25 min under OGTT at 5 g, single-phase LT and LT difference at 1118 $cm^{-1}$ of 10 min under OGTT at 20 g, bi-phase LTs and LT differences at 1118 $cm^{-1}$ of 5 min and 25 min under OGTT at 75 g, bi-phase LTs and LT differences at 1153 $cm^{-1}$ of 35 min and 50 min under OGTT at 5 g, single-phase LT and LT difference at 1153 $cm^{-1}$ of 10 min and 15 min under OGTT at 20 g, single-phase LT and LT difference at 1153 $cm^{-1}$ of 30 min under OGTT at 75 g, the longest durations of LT differences of 5 min and 30 min for dose 75 g, 10 min for dose 20 g, and 15 min and 30 min for dose 5 g at 1030-1041 $cm^{-1}$, 5 min for dose 75 g, 0 min and 10 min, and 20 min for dose 20 g, and 15 min and 30 min for dose 5 g at 1080 $cm^{-1}$, 5 min and 25 min for dose 75 g, 10 min for dose 20 g, and 10 min and 25 min for dose 5 g at 1118 $cm^{-1}$, 10 min for dose 75 g, 10 min and 15 min for dose 20 g, and 35 min and 50 min at 1153 $cm^{-1}$ under OGTT with different doses, dose-independent LTs and LT differences for each assigned glucose-specific peak under any OGTT with different doses of 5 g, 20 g or 75 g, bi-phase LTs with LT differences of 15 min and 30 min at 1030-1041 $cm^{-1}$, 15 min and 30 min at 1080 $cm^{-1}$, 10 min and 25 min at 1118 $cm^{-1}$, 35 min and 50 min at 1153 $cm^{-1}$ under OGTT at 5 g, single-, bi-phase, and cascading multi-phase LTs with LT differences of 10 min at 1030-1041 $cm^{-1}$, 0 min and 10 min, and 20 min at 1080 $cm^{-1}$, 10 min at 1118 $cm^{-1}$, 10 min and 15 min at 1153 $cm^{-1}$ under OGTT at 20 g, single- and bi-phase LTs with LT differences of 5 min and 30 min at 1030-1041 $cm^{-1}$, 5 min at 1080 $cm^{-1}$, 5 min and 25 min at 1118 $cm^{-1}$, 10 min at 1153 $cm^{-1}$ under OGTT at 75 g, the longest durations of LT differences of starting from 5 min-50 min with single-, bi-, or cascading multi-phase appearances at 1030-1041 $cm^{-1}$, 1080 $cm^{-1}$, 1118 $cm^{-1}$, and 1153 cm-under OGTT at 75 g in a healthy subject, as compared with the shortest durations of LT differences of starting from 0 min-30 min with single-phase appearances at 1030-1041 $cm^{-1}$, 1080 $cm^{-1}$, 1118 $cm^{-1}$, and 1153 $cm^{-1}$ under OGTT at 75 g in a diabetic subject, and as compared with the shortest durations of LT differences of starting from 0 min-55 min with cascading multi-phase appearances at 1030-1041 $cm^{-1}$, 1080 $cm^{-1}$, 1118 $cm^{-1}$, and 1153 $cm^{-1}$ under OGTT at 75 g in a prediabetic subject, to be specific for a healthy subject,
the spectral pattern characterized by
  cascading multi-phase LTs and LT differences at 1030-1041 cm$^{-1}$ of 5 min, 20 min, 30 min and 45 min under OGTT at 75 g,
  cascading multi-phase LTs and LT differences at 1080 cm$^{-1}$ of 5 min, 20 min, and 45 min under OGT at 75 g,
  cascading multi-phase LTs and LT differences at 1118 cm$^{-1}$ of 5 min, 20 min, 30 min, and 40 min under OGTT at 75 g,
  cascading multi-phase LTs and LT differences at 1153 cm$^{-1}$ of 0 min, 15 min, 25 min, and 55 min under OGTT at 75 g,
  cascading multi-phase LTs and LT differences of 5 min-45 min at 1030-1041 cm$^{-1}$, 5 min-45 min at 1080 cm$^{-1}$, 5 min-40 min at 1118 cm$^{-1}$, 0 min-55 min at 1153 cm$^{-1}$ under OGTT at 75 g,
  dose-independent LTs and LT differences with cascading multi-phase appearances at
  5 min, 20 min, 30 min and 45 min at 1030-1041 cm$^{-1}$,
  5 min, 20 min and 45 min at 1080 cm$^{-1}$,
  5 min, 20 min, 30 min and 40 min at 1118 cm$^{-1}$,
  0 min, 15 min, 25 min and 55 min at 1153 cm$^{-1}$
  under OGTT at 75 g,
  the shortest durations of LT differences of starting from 0 min with cascading multi-phase appearances at 1030-1041 cm$^{-1}$, 1080 cm$^{-1}$, 1118 cm$^{-1}$, and 1153 cm$^{-1}$ under OGTT at 75 g, as compared with the shortest durations of LT differences of starting from 0 min with single-phase appearances at 1030-1041 cm$^{-1}$, 1080 cm$^{-1}$, 1118 cm$^{-1}$, and 1153 cm$^{-1}$ under OGTT at 75 g in a diabetic subject, and as compared with the longest durations of LT differences of starting from 5 min with single-, bi- or cascading multi-phase appearances at 1030-1041 cm$^{-1}$, 1080 cm$^{-1}$, 1118 cm$^{-1}$, and 1153 cm$^{-1}$ under OGTT at 75 g in a healthy subject,
to be specific for a prediabetic subject, and
the spectral pattern characterized by
  bi-phase LTs and LT differences of 0 min and 10 min at 1030-1041 cm$^{-1}$ under OGTT at 5 g,
  single-phase LT and LT difference of 0 min at 1030-1041 cm$^{-1}$ under OGTT at 20 g,
  single-phase LT and LT difference of 0 min at 1030-1041 cm$^{-1}$ under OGTT at 75 g,
  single-phase LT and LT difference of 10 min at 1080 cm$^{-1}$ under OGTT at 5 g,
  single-phase LT and LT difference of 15 min at 1080 cm$^{-1}$ under OGTT at 20 g,
  single-phase LT and LT difference of 0 min at 1080 cm$^{-1}$ under OGTT at 75 g,
  cascading multi-phase LTs and LT differences of 0 min, 10 min and 25 min at 1118 cm$^{-1}$ under OGTT at 5 g,
  single-phase LT and LT difference of 5 min at 1118 cm$^{-1}$ under OGTT at 20 g,
  single-phase LT and LT difference of 0 min at 1118 cm$^{-1}$ under OGTT at 75 g,
  bi-phase LTs and LT differences of 15 min and 25 min under OGTT at 5 g,
  bi-phase LTs and LT differences of 25 min and 40 min under OGTT at 20 g,
  single-phase LT and LT differences of 30 min under OGTT at 75 g,
  the shortest durations of LT differences of
  0 min for dose 75 g, 0 min for dose 20 g, 0 min and 10 min for dose 5 g at 1030-1041 cm$^{-1}$,
  0 min for dose 75 g, 15 min for dose 20 g, 10 min for dose 5 g at 1080 cm$^{-1}$,
  0 min for dose 75 g, 5 min for dose 20 g, 0 min and 10 min and 25 min for dose 5 g at 1118 cm$^{-1}$,
  30 min for dose 75 g, 25 min and 40 min for dose 20 g, 15 min and 25 min at 1153 cm$^{-1}$
  under OGTT with different doses,
  the shortest durations of LTs and LT differences of
  0 min at 1030-1041 cm$^{-1}$,
  0 min, 0 min and 60 min, or 60 min at 1080 cm$^{-1}$,
  0 min or 0 min and 60 min at 1118 cm$^{-1}$,
  30 min and 60 min at 1153 cm$^{-1}$
  under post-prandial glucose test,
  dose-dependent LTs and LT differences at 1030-1041 cm$^{-1}$, 1080 cm$^{-1}$, and 1118 cm-under any OGTT with different doses at 5 g, 20 g, and 75 g glucose,
  single-, bi-phase, and cascading multi-phase LTs and LT differences of 0 min and 10 min at 1030-1041 cm$^{-1}$, 10' at 1080 cm$^{-1}$, 0 min, 10 min and 25 min at 1118 cm$^{-1}$, 15 min and 25 min at 1153 cm$^{-1}$ under OGTT at 5 g,
  single- and bi-phase LTs and LT differences of 0 min at 1030-1041 cm$^{-1}$, 15' at 1080 cm$^{-1}$, 5' at 1118 cm$^{-1}$, 15' and 40' at 1153 cm$^{-1}$ under OGTT at 20 g,
  single-phase LT and LT differences of 0' at 1030-1041 cm$^{-1}$, 0' at 1080 cm$^{-1}$, 0' at 1118 cm$^{-1}$, 30' at 1153 cm$^{-1}$ under OGTT at 75 g,
  the shortest durations of LT differences of starting from 0 min-30 min with single-phase appearances at 1030-1041 cm$^{-1}$, 1080 cm$^{-1}$, 1118 cm$^{-1}$, and 1153 cm$^{-1}$ under OGTT at 75 g, as compared with the shortest durations of LT differences of starting from 0 min with cascading multi-phase appearances at 1030-1041 cm$^{-1}$, 1080 cm$^{-1}$, 1118 cm$^{-1}$, and 1153 cm$^{-1}$ under OGTT at 75 g in a prediabetic subject, and as compared with the longest durations of LT differences of starting from 5 min with single-, bi- or cascading multi-phase appearances at 1030-1041 cm$^{-1}$, 1080 cm$^{-1}$, 1118 cm$^{-1}$, and 1153 cm$^{-1}$ under OGTT at 75 g in a healthy subject,
to be specific for a diabetic subject with type 2.

3. The method of claim 1, for monitoring the change of the spectral pattern of individual metabolic response and generated predictive clinical metrics on HATR-FTIR spectroscopy for healthy, prediabetic, and diabetic subjects under post-prandial glucose test or OGTT with different doses at 5 g, 20 g, and 75 g.

4. The method of claim 1, for diagnosing disorders of glucose metabolism including prediabetes and diabetes in a subject, or for screening and follow-up a development of a diabetes in a healthy subject, or for screening and follow-up a development of a diabetes in a subject with a prediabetes, or for predicting the subject's risk of hyperglycemia, or for staging type 2 diabetes in a subject, or for managing a subject with or without hyperglycemia, or for assessing the quality of metabolic control in a subject, or for determining an effective therapy in a subject with a type 2 diabetes, or for determining an effective dosage of drug in a subject with a type 2 diabetes, or for stratifying a subject to a therapeutic regimen for treating or preventing a diabetes by determining prognosis of the treatment in prediabetic and diabetic subject.

5. FTIR spectrometer when used in a method for diagnosing disorders of glucose metabolism including prediabetes and diabetes in a subject, or for screening and follow-up a development of a diabetes in a healthy subject, or for screening and follow-up a development of a diabetes in a subject with a prediabetes, or for predicting the subject's risk of hyperglycemia, or for staging type 2 diabetes in a subject, or for managing a subject with or without hyperglycemia, or for assessing the quality of metabolic control in a subject, or for determining an effective therapy in a subject with a type 2 diabetes, or for determining an effective dosage of drug in a subject with a type 2 diabetes, or for stratifying a subject to a therapeutic regimen for treating or preventing a diabetes by determining prognosis of the treatment in prediabetic and diabetic subject, comprising the steps according to claim 1.

6. A method for in vivo glucose molecule characterization at 1030 cm$^{-1}$ or 1041 cm$^{-1}$, characterized by spectral bounded bands within 1030-1041 cm$^{-1}$ in HATR-FTIR spectra corresponding to identity and structures to glucose molecules in correlation with characteristic measurements of the peak position and its shift, the peak levels measured in the interstitial fluid of the epidermal skin tissue of a healthy, prediabetic or diabetic subject under post-prandial glucose test or OGTT with different doses at 5 g, 20 g, and 75 g by HATR-FTIR spectroscopy, comprising:
  characterizing a glucose molecule in HATR-FTIR spectra by
    predominant mean peak position at 1037-1041 cm$^{-1}$ within 1030-1041 cm$^{-1}$,
    the highest glucose peak levels within 1030-1041 cm$^{-1}$ similar to the peak levels at 1118 cm$^{-1}$ in HATR-FTIR spectra,
    dose-dependent peak levels to high doses of glucose under OGTT at 75 g,
    cascading multi-phase LTs and LT differences of 5 min, 20 min, 30 min, and 45 min under OGTT at 75 g,
  to be specific for a prediabetic subject; and
  (i) characterizing a glucose molecule in HATR-FTIR spectra by
    predominant mean peak position at 1030 cm$^{-1}$ within 1030-1041 cm$^{-1}$,
    the highest glucose peak levels within 1030-1041 cm$^{-1}$ over the other glucose peaks levels at 1080 cm$^{-1}$, 1118 cm$^{-1}$, and 1153 cm$^{-1}$,
    independent to low, medium, and high glucose doses peak levels under OGTT with 5 g, 20 g, and 75 g,
    bi-phase LTs and LT differences of 15 min and 30 min under OGTT at 5 g,
    single-phase LTs and LT differences of 10 min under OGTT at 20 g,
    bi-phase LTs and LT differences of 5 min and 30 min under OGTT at 75 g,
  to be specific for a healthy subject; or
  (ii) characterizing a glucose molecule in HATR-FTIR spectra by
    predominant mean peak position at 1039-1041 cm$^{-1}$ within 1030-1041 cm$^{-1}$ in HATR-FTIR spectra,
    dose-dependent to low, medium, and high glucose doses peak levels under OGTT with 5 g, 20 g, and 75 g,
    single-phase LT and LT difference of 0 min under post-prandial glucose test,
    bi-phase LTs and LT differences of 0 min and 10 min under OGTT at 5 g,
    single-phase LT and LT difference of 0 min under OGTT at 20 g,
    single-phase LT and LT difference of 0 min under OGT at 75 g,
  to be specific for a diabetic subject.

7. A method for in vivo glucose molecule characterization at 1080 cm$^{-1}$, characterized by spectral bounded bands at 1080 cm$^{-1}$ in HATR-FTIR spectra corresponding to identity and structures to glucose molecules in correlation with characteristic measurements of the peak position and its shift, the peak levels measured in the interstitial fluid of the epidermal skin tissue of a healthy, prediabetic or diabetic subject under post-prandial glucose test or OGTT with different doses at 5 g, 20 g, and 75 g by HATR-FTIR spectroscopy, comprising:
  characterizing a glucose molecule in HATR-FTIR spectra by dose-dependent peak levels to high glucose dose under OGTT with 75 g,
    cascading multi-phase LTs and LT differences of 5 min, 20 min, and 45 min under OGTT at 75 g,
  to be specific for a prediabetic subject; and
  (i) characterizing a glucose molecule in HATR-FTIR spectra by
    dose-independent peak levels to low, medium, and high glucose doses under OGTT with 5 g, 20 g, and 75 g,
    bi-phase LTs and LT differences of 15 min and 30 min under OGTT at 5 g,
    cascading multi-phase LTs and LTs differences of 0 min, 10 min, and 20 min under OGTT at 20 g,
    single-phase LT and LT difference of 5 min under OGTT at 75 g, to be specific for a healthy subject; or
  (ii) characterizing a glucose molecule in HATR-FTIR spectra by
    dose-dependent peak levels to low, medium, and high glucose doses under OGTT with 5 g, 20 g, and 75 g,
    single-phase LT and LT difference of 10 min under OGTT at 5 g,
    single-phase LT and LT difference of 15 min under OGTT at 20 g,
    single-phase LT and LT difference of 0 min under OGTT at 75 g,
  to be specific for a diabetic subject.

8. A method for in vivo glucose molecule characterization at 1118 cm$^{-1}$, characterized by spectral bounded bands at 1118 cm$^{-1}$ in HATR-FTIR spectra corresponding to identity and structures to glucose molecules in correlation with characteristic measurements of the peak position and its shift, the peak levels measured in the interstitial fluid of the epidermal skin tissue of a healthy, prediabetic or diabetic subject under post-prandial glucose test or OGTT with different doses at 5 g, 20 g, and 75 g by HATR-FTIR spectroscopy, comprising:
  characterizing a glucose molecule in HATR-FTIR spectra by
    predominant right-shifted mean peak position within 1120-1122 cm$^{-1}$,
    the highest glucose peak levels similar to glucose peak levels at 1030-1041 cm$^{-1}$ over the other 2 glucose peak levels at 1080 cm$^{-1}$ and 1153 cm$^{-1}$,
    dose-independent peak levels to high dose of glucose at 75 a under OGTT at 75 g,
    cascading multi-phase LT's and LT differences with the time intervals of 5 min, 20 min, 30 min and 40 min under OGTT at 75 g,
  to be specific for a prediabetic subject; and
  (i) characterizing a glucose molecule in HATR-FTIR spectra by
    predominant left-shifted mean peak position within 1114-1118 cm$^{-1}$, wherein mean peak position at 1118 cm$^{-1}$ is characteristic under OGTT at 5 g, mean peak position at 1114-1118 cm$^{-1}$ is characteristic under OGTT at 20 g, mean peak position at 1116-1118 cm$^{-1}$ is characteristic under OGTT at 75 g,
    dose-independent peak levels to low, medium, and high glucose doses under OGTT with 5 g, 20 g, and 75 g,
    bi-phase LTs and LT differences of 10 min and 25 min under OGTT at 5 g,
    single-phase LT and LT difference of 10 min under OGTT at 20 g, bi-phase LT's and LT differences of 5 min and 25 min under OGTT at 75 g, to be specific for a healthy subject; or
(ii) characterizing a glucose molecule in HATR-FTIR spectra by
dominant right-shifted mean peak position at 1120-1122 $cm^{-1}$,
the highest glucose peak levels within 1120-1122 $cm^{-1}$ over glucose peaks levels at 1030-1041 $cm^{-1}$, 1080 $cm^{-1}$, and 1153 $cm^{-1}$ in HATR-FTIR spectra,
dose-dependent peak levels to low, medium, and high doses of glucose at 5 g, 20 g, and 75 g under OGTT at 5 g, 20 g, and 75 g,
three-phase LT's and LT differences of 0 min, 10 min and 25 min under OGTT at 5 g,
single-phase LTs and LT differences of 5 min under OGTT at 20 g,
single-phase LT and LT differences of 0 min under OGTT at 75 g,
to be specific for a diabetic subject.

9. A method for in vivo glucose molecule characterization at 1153 $cm^{-1}$, characterized by spectral bounded bands at 1153 $cm^{-1}$ in HATR-FTIR spectra corresponding to identity and structures to glucose molecules in correlation with characteristic measurements of the peak position and its shift, the peak levels measured in the interstitial fluid of the epidermal skin tissue of a healthy, prediabetic or diabetic subject under post-prandial glucose test or OGTT with different doses at 5 g, 20 g, and 75 g by HATR-FTIR spectroscopy, comprising:
characterizing a glucose molecule in HATR-FTIR spectra by
the lowest glucose peak levels within 1153 $cm^{-1}$ below glucose peak levels at 1030-1041 $cm^{-1}$, 1080 $cm^{-1}$, and 1118 $cm^{-1}$,
cascading LT's and LT differences of 0 min, 15 min, 25 min and 55 min under OGTT at 75 g,
to be specific for a prediabetic subject; and
(i) characterizing a glucose molecule in HATR-FTIR spectra by
predominant left-shifted mean peak position within 1149-1153 $cm^{-1}$,
the lowest glucose peak levels within 1153 $cm^{-1}$ below glucose peaks levels at 1030-1041 $cm^{-1}$, 1080 $cm^{-1}$ and 1118 $cm^{-1}$,
bi-phase LTs and LT differences of 35 min and 50 min under OGTT at 5 g,
bi-phase LTs and LT differences with the time intervals of 10 min and 15 min under OGTT at 20 g,
single-phase LT and LT difference of 10 min under OGTT at 75 g,
to be specific for a healthy subject; or
(ii) characterizing a glucose molecule in HATR-FTIR spectra by
predominant right-shifted mean peak position within 1153-1157 $cm^{-1}$,
the lowest glucose peak levels within 1153 $cm^{-1}$ below glucose peak levels at 1030-1041 $cm^{-1}$, 1080 $cm^{-1}$, and 1118 $cm^{-1}$,
bi-phase LTs and LT differences of 15 min and 25 min under OGTT at 5 g,
bi-phase LTs and LT differences of 25 min and 40 min under OGTT at 20 g,
single-phase LT and LT difference of 30 min under OGT at 75 g,
to be specific for a diabetic subject.

10. A method for in vivo glucose molecule characterization of a combination group of glucose molecules with characteristic spectral parameters at consistent and significant absorption wave number at 1030 $cm^{-1}$, 1041 $cm^{-1}$, 1080 $cm^{-1}$, 1118 $cm^{-1}$, and 1153 $cm^{-1}$, characterized by spectral bounded bands at 1030-1041 $cm^{-1}$ 1080 $cm^{-1}$, 1118 $cm^{-1}$, and 1153 $cm^{-1}$ in HATR-FTIR spectra corresponding to identity and structures to glucose molecules in correlation with characteristic measurements of the peak position and its shift, the peak levels measured in the interstitial fluid of the epidermal skin tissue of a healthy, prediabetic or diabetic subject under post-prandial glucose test or OGTT with different doses at 5 g, 20 g, and 75 g by HATR-FTIR spectroscopy, comprising:
characterizing a combination group of glucose molecules in HATR-FTIR spectra by
cascading multi-phase LTs and LT differences at 1030-1041 $cm^{-1}$ of 5 min, 20 min, 30 min, and 45 min under OGTT at 75 g,
cascading multi-phase LTs and LT differences at 1080 $cm^{-1}$ of 5 min, 20 min, and 45 min under OGTT at 75 g,
cascading multi-phase LTs and LT differences at 1118 $cm^{-1}$ of 5 min, 20 min, 30 min, and 40 min under OGTT at 75 g,
cascading multi-phase LTs and LT differences at 1153 $cm^{-1}$ of 0 min, 15 min, 25 min, and 55 min under OGT at 75 g,
cascading multi-phase LTs and LT differences of 5 min-45 min at 1030-1041 $cm^{-1}$, 5 min-45 min at 1080 $cm^{-1}$, 5 min-40 min at 1118 $cm^{-1}$, 0 min-55 min at 1153 $cm^{-1}$ under OGT at 75 g,
dose-independent LTs and LT differences with cascading multi-phase appearances at
5 min, 20 min, 30 min and 45 min at 1030-1041 $cm^{-1}$,
5 min, 20 min and 45 min at 1080 $cm^{-1}$,
5 min, 20 min, 30 min and 40 min at 1118 $cm^{-1}$,
0 min, 15 min, 25 min and 55 min at 1153 $cm^{-1}$
under OGT at 75 g,
the shortest durations of LT differences of starting from 0 min with cascading multi-phase appearances at 1030-1041 $cm^{-1}$, 1080 $cm^{-1}$, 1118 $cm^{-1}$, and 1153 $cm^{-1}$ under OGTT at 75 g, as compared with the shortest durations of LT differences starting from 0 min with singe-phase appearances at 1030-1041 $cm^{-1}$, 1080 $cm^{-1}$, 1118 $cm^{-1}$, and 1153 $cm^{-1}$ under OGTT at 75 g in a diabetic subject, and as compared with the longest durations of LT differences starting from 5 min with single-, bi- or cascading multi-phase appearances at 1030-1041 $cm^{-1}$, 1080 $cm^{-1}$, 1118 $cm^{-1}$, and 1153 $cm^{-1}$ under OGTT at 75 g in a healthy subject,
to be specific for a prediabetic subject; and
(i) characterizing a combination group of glucose molecules in HATR-FTIR spectra by
bi-phase LTs and LT differences at 1030-1041 $cm^{-1}$ of 15 min and 30 min under OGTT at 5 g,
single-phase LTs and LT differences at 1030-1041 $cm^{-1}$ of 10 min under OGTT at 20 g,
bi-phase LTs and LT differences with CBG at 1030-1041 $cm^{-1}$ of 5 min and 30 min under OGTT at 75 g,
bi-phase LTs and LT differences at 1080 $cm^{-1}$ of 15 min and 30 min under OGTT at 5 g,
three-phase LTs and LT differences at 1080 $cm^{-1}$ of 0 mm, 10 min, and 20 min under OGTT at 20 g, single-phase LTs and LT differences with CBG at 1080 cm$^{-1}$ of 5 mi under OGTT at 75 g,
bi-phase LTs and LT differences at 1118 cm$^{-1}$ of 10 min and 25 min under OGTT at 5 g,
single-phase LT and LT difference at 1118 cm$^{-1}$ of 10 min under OGTT at 20 g,
bi-phase LTs and LT differences at 1118 cm$^{-1}$ of 5 min and 25 min under OGTT at 75 g,
bi-phase LTs and LT differences at 1153 cm$^{-1}$ of 35 min and 50 min under OGTT at 5 g,
single-phase LT and LT difference at 1153 cm$^{-1}$ of 10 min and 15 min under OGTT at 20 g,
single-phase LT and LT difference at 1153 cm$^{-1}$ of 30 min under OGTT at 75 g,
the longest durations of LT differences of
5 min and 30 mm for dose 75 g, 10 mm for dose 20 g and 15 min, and 30 min for dose 5 g at 1030-1041 cm$^{-1}$,
5 min for dose 75 g, 0 min and 10 min and 20 min for dose 20 g and 15 min, and 30 min for dose 5 g at 1080 cm$^{-1}$,
5 min and 25 min for dose 75 g, 10 min for dose 20 g and 10 min, and 25 min for dose 5 g at 1118 cm$^{-1}$,
10 min for dose 75 g, 10 min and 15 min for dose 20 g, and 35 min and 50 min for dose 5 g at 1153 cm$^{-1}$
under OGT with different doses,
dose-independent LTs and LT differences for each assigned glucose-specific peak under any OGTT with different doses of 5 g, 20 g or 75 g,
bi-phase LTs with LT differences of 15 min and 30 min at 1030-1041 cm$^{-1}$, 15 min and 30 min at 1080 cm$^{-1}$, 10 min and 25 min at 1118 cm$^{-1}$, 35 min and 50 min at 1153 cm$^{-1}$ under OGTT at 5 g,
single-, bi-phase, and cascading multi-phase LTs with LT differences of 10 min at 1030-1041 cm$^{-1}$, 0 min and 10 min, and 20 min at 1080 cm$^{-1}$, 10 min at 1118 cm$^{-1}$, 10 min and 15 min at 1153 cm$^{-1}$ under OGTT at 20 g,
single- and bi-phase LTs with LT differences of 5 min and 30 min at 1030-1041 cm$^{-1}$, 5 min at 1080 cm$^{-1}$, 5 min and 25 min at 1118 cm$^{-1}$, 10 min at 1153 cm$^{-1}$ under OGTT at 75 g,
the longest durations of LT differences starting from 5 min with single-, bi- or cascading multi-phase appearances at 1030-1041 cm$^{-1}$, 1080 cm$^{-1}$, 1118 cm$^{-1}$, and 1153 cm$^{-1}$ under OGTT at 75 g in a healthy subject, Table 4 (column 2) or Table 7 (column 2), as compared with the shortest durations of LT differences starting from 0 min with single-phase appearances at 1030-1041 cm$^{-1}$, 1080 cm$^{-1}$, 1118 cm$^{-1}$, and 1153 cm$^{-1}$ under OGTT at 75 g in a diabetic subject, and as compared with the shortest durations of LT differences of starting from 0 min with cascading multi-phase appearances at 1030-1041 cm$^{-1}$, 1080 cm$^{-1}$, 1118 cm$^{-1}$, and 1153 cm$^{-1}$ under OGTT at 75 g in a prediabetic subject,
to be specific for a healthy subject, or
(ii) characterizing a combination group of glucose molecules in HATR-FTIR spectra by
bi-phase LTs and LT differences of 0 min and 10 min at 1030-1041 cm$^{-1}$ under OGTT at 5 g,
single-phase LT and LT difference of 0 min at 1030-1041 cm$^{-1}$ under OGTT at 20 g,
single-phase LT and LT difference of 0 min at 1030-1041 cm$^{-1}$ under OGT at 75 g,
single-phase LT and LT difference of 10 min at 1080 cm$^{-1}$ under OGTT at 5 g,
single-phase LT and LT difference of 15 min at 1080 cm$^{-1}$ under OGTT at 20 g,
single-phase LT and LT difference of 0 min at 1080 cm$^{-1}$ under OGTT at 75 g,
cascading multi-phase LTs and LT differences of 0 min, 10 min and 25 min at 1118 cm$^{-1}$ under OGTT at 5 g,
single-phase LT and LT difference of 5 min at 1118 cm$^{-1}$ under OGTT at 20 g,
single-phase LT and LT difference of 0 min at 1118 cm$^{-1}$ under OGTT at 75 g,
bi-phase LTs and LT differences of 15 min and 25 min under OGTT at 5 g,
bi-phase LTs and LT differences of 25 min and 40 min under OGTT at 20 g,
single-phase LT and LT differences of 30 min under OGTT at 75 g,
the shortest durations of LT differences of
0 min for dose 75 g, 0 min for dose 20 g, 0 min and 10 min for dose 5 g at 1030-1041 cm$^{-1}$,
0 min for dose 75 g, 15 min for dose 20 g, 10 min for dose 5 g at 1080 cm$^{-1}$,
0 min for dose 75 g, 5 min for dose 20 g, 0 min, and 10 min, and 25 min for dose 5 g at 1118 cm$^{-1}$,
30 min for dose 75 g, 25 min and 40 min for dose 20 g, and 15 min and 25 min at 1153 cm$^{-1}$
under OGTT with different doses,
the shortest durations of LTs and LT differences of
0 min at 1030-1041 cm$^{-1}$,
0 min, 0 min and 60 min or 60 min at 1080 cm$^{-1}$,
0 min or 0 min and 60 min at 1118 cm$^{-1}$,
30 min and 60 min at 1153 cm$^{-1}$
under post-prandial glucose test,
dose-dependent LTs and LT differences at 1030-1041 cm$^{-1}$, 1080 cm$^{-1}$ and 1118 cm$^{-1}$ under any OGTT with different doses at 5 g, 20 g, and 75 g glucose,
single-, bi-phase, and cascading multi-phase LTs and LT differences of 0 min and 10 min at 1030-1041 cm$^{-1}$, 10' at 1080 cm$^{-1}$, 0 min, 10 min and 25 min at 1118 cm$^{-1}$, 15 min and 25 min at 1153 cm$^{-1}$ under OGTT at 5 g,
single- and bi-phase LTs and LT differences of 0 min at 1030-1041 cu, 15' at 1080 cm$^{-1}$, 5' at 1118 cm$^{-1}$, 15' and 40' at 1153 cm$^{-1}$ under OGTT at 20 g,
single-phase LT and LT differences of 0' at 1030-1041 cm$^{-1}$, 0' at 1080 cm$^{-1}$, 0' at 1118 cm$^{-1}$, 30' at 1153 cm$^{-1}$ under OGTT at 75 g,
the shortest durations of LT differences starting from 0 min with single-phase appearances at 1030-1041 cm$^{-1}$, 1080 cm$^{-1}$, 1118 cm$^{-1}$, and 1153 cm$^{-1}$ under OGTT at 75 g, as compared with the shortest durations of LT differences starting from 0 min with cascading multi-phase appearances at 1030-1041 cm$^{-1}$, 1080 cm$^{-1}$, 1118 cm$^{-1}$, and 1153 cm$^{-1}$ under OGT at 75 g in a prediabetic subject, and as compared with the longest durations of LT differences starting from 5 min with single-, bi- or cascading multi-phase appearances at 1030-1041 cm$^{-1}$, 1080 cm$^{-1}$, 1118 cm$^{-1}$, and 1153 cm$^{-1}$ under OGT at 75 g in a healthy subject,
to be specific for a diabetic subject with type 2.

11. The method of any of claim 6 diagnosing disorders of glucose metabolism including prediabetes and diabetes in a subject, or for screening and follow-up a development of a diabetes in a healthy subject, or for screening and follow-up a development of a diabetes in a subject with a prediabetes, or for predicting the subject's risk of hyperglycemia, or for staging type 2 diabetes in a subject, or for managing a subject with or without hyperglycemia, or for assessing the quality of metabolic control in a subject, or for determining an effective therapy in a subject with a type 2 diabetes, or for determining an effective dosage of drug in a subject with a type 2 diabetes, or for stratifying a subject to a therapeutic regimen for treating or preventing a diabetes by determining prognosis of the treatment in prediabetic and diabetic subject.

12. The method of any of claim 6, wherein LT is the time interval from the time-point of induction of glucose excursions till the time-point of maximum detected levels of the glucose-specific peaks at 1030-1041 $cm^{-1}$, 1080 $cm^{-1}$, 1118 $cm^{-1}$, and 1153 $cm^{-1}$ on HATR-FTIR spectrometer in the interstitial fluid of skin tissue in gathered HATR-FTIR spectra from the forearm of a tested subject under postprandial glucose test or OGTT with different doses at 5 g, 20 g, and 75 g.

* * * * *